United States Patent [19]

Batchelor et al.

[11] Patent Number: 5,403,934
[45] Date of Patent: Apr. 4, 1995

[54] HETEROCYCLIC COMPOUNDS

[75] Inventors: John F. Batchelor; Clive L. Yeates, both of Beckenham, England

[73] Assignee: Burroughs Wellcome Co., Research Triangle Park, N.C.

[21] Appl. No.: 275,668

[22] Filed: Jul. 15, 1994

Related U.S. Application Data

[63] Continuation of Ser. No. 934,673, filed as PCT/GB91/00380, Mar. 11, 1991, published as WO91/13873, Sep. 19, 1991, abandoned.

[30] Foreign Application Priority Data

Mar. 12, 1990 [GB] United Kingdom ............... 9005518

[51] Int. Cl.⁶ ............... C07D 211/82; C07D 211/86; C07D 211/92; C07D 213/68
[52] U.S. Cl. ........................... 546/290; 546/296
[58] Field of Search ............. 546/290, 296; 514/340, 514/344, 345

[56] References Cited

U.S. PATENT DOCUMENTS

| | | | |
|---|---|---|---|
| 3,206,358 | 9/1965 | Stevenson | 167/53 |
| 4,235,619 | 11/1980 | Taylor | 71/66 |
| 5,245,035 | 9/1993 | Thomas | 546/153 |

FOREIGN PATENT DOCUMENTS

| | | |
|---|---|---|
| 0123239 | 10/1984 | European Pat. Off. . |
| 0304057 | 2/1989 | European Pat. Off. . |
| 1451373 | 6/1965 | France . |
| 2162238 | of 0000 | Germany . |
| 2014779 | 10/1970 | Germany . |
| 52-87171 | 7/1977 | Japan . |
| 2029403 | 3/1980 | United Kingdom . |

OTHER PUBLICATIONS

Chem. Abs vol 104 No. 183468S 1986 p. 376 "Photosynthetic electron transport inhibition . . . relationships" Asami et al.

(List continued on next page.)

Primary Examiner—C. Warren Ivy
Assistant Examiner—D. Margaret M. Mach
Attorney, Agent, or Firm—Nixon & Vanderhye

[57] ABSTRACT

A compound of formula (I):

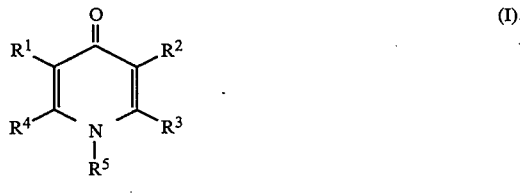

wherein
$R^1$ represents a hydrogen or halogen atom, or a cyano group;
$R^2$ represents an optionally substituted carbocyclic group having 6 to 10 ring atoms and containing at least one aromatic ring; an optionally substituted heterocyclic group having 5 to 10 ring atoms, including 1 to 4 heteroatoms selected from O, N and S, and containing at least one aromatic ring; or an optionally substituted $C_{3-6}$cycloalkyl, $C_{3-6}$cycloalkyl-$C_{1-6}$alkyl, or $C_{1-10}$alkyl group;
$R^3$ and $R^4$, which may be the same or different, each represent a hydrogen or halogen atom, or a $C_{1-6}$alkyl group optionally substituted by 1 to 3 halogen atoms; and
$R^5$ represents a hydrogen atom, a hydroxyl group, or a $C_{1-6}$alkyl group, optionally substituted by hydroxy, carboxy, amino or mono- or di-($C_{1-4}$)alkyl amino, and salts and other physiologically functional derivative thereof.

The compounds are useful in the treatment of parasitic infections eg. malaria, coccidiosis and *Pneumocystis carinii* pneumonia.

15 Claims, No Drawings

OTHER PUBLICATIONS

Abs vol 66 No. 55339k 1967 p. 5221 Vartanyan et al "Mutual transformations of heterocycles containing S, N, O".

Chem. Abs. vol 100 No. 22811a 1984 p. 508 DeMarch et al "Metal complexes in organic synthesis . . . catalysis".

Chem. Abs. vol. 88 No. 169977b 1978 p. 577 Yoshida et al "γ-pyridone derivatives".

Chem. Abs. vol. 87, No. 95448k 1977 p. 27 Kato et al "Antitumor activity of compounds derived from diketene . . . ".

Chem. Abs. vol. 86 No. 106483a 1977 p. 501 Kato et al "Studies on ketene and its derivatives".

Chem. Abs. vol. 71 No. 38938r 1969 p. 292 Makikaku et al "Furo[3,2-c] pyridines".

J. Am. Chem. Soc. vol. 95, No. 23, 1973 p. 7914 "Photochemical Rearrangements of Neutral . . . Pyronens".

Agr. Biol. Chem. vol. 50 No. 2 469–474 1986 Asami et al "Photosyntehtic Electron Tranport . . . Relationships".

Chem. Pharm. Bull. vol. 24 No. 10 pp. 2549–2552 Kato et al "Studies on Ketene and Its Derivatives . . . ".

Chem. Pharm. Bull. vol. 29 No. 4 (1981) pp. 1044–1048 "Studies on Quinoline and Isoquinoline . . . ".

Kato et al, Chemical Abstracts #95448k, vol. 87, 1977.

*J. Am. Chem. Soc.,* 96:4, N. Ishibe, pp. 1152–1158, Feb. 20, 1974.

*Chem. Abs.,* vol. 87, #95448k, Kato, Tetsuzo, et al, 1977. (Prior Art–Other Documents #5).

*Advanced, Organic Chem.* 3rd Ed., Jerry March, 1985, pp. 476–477, 321, 68–69.

HETEROCYCLIC COMPOUNDS

This is a continuation of application Ser. No. 07/934,673, filed as PCT/GB91/00380, Mar. 11, 1991, published as WO 91/13873, Sep. 19, 1991, now abandoned.

The present invention relates to heterocyclic compounds and their use in chemotherapy. More specifically this invention is concerned with certain 4-pyridone derivatives, processes for their preparation, pharmaceutical formulations thereof and their use in the chemotherapy of certain parasitic infections.

A group of 3,5-dihalo-2,6-dialkyl-4-pyridinol derivatives (the tautomeric form of 4-pyridones) is described in U.S. Pat. No. 3,206,358 as having anticoccidial activity.

European Patent Application No. 123239 discloses combinations of the aforementioned 4-pyridinol derivatives with antiprotozoal naphthoquinones, e.g. antimalarial naphthoquinones, in a potentiating ratio.

Parasitic protozoal infections are responsible for a wide variety of diseases of medical and veterinary importance, including malaria in man and various coccidioses in birds, fish and mammals. Many of the diseases are life-threatening to the host and cause considerable economic loss in animal husbandry. Parasitic protozoa include the Apicomplexa, such as species of Eimeria, Theileria, Babesia, Cryptosporidium, Toxoplasma, and Plasmodium; and the Mastigophora such as species of Leishmania. Another parasitic organism of increasing concern is *Pneumocystis carinii*, which can cause an often-fatal pneumonia in immunodeficient or immunocompromised hosts, including those infected with HIV. The classification of this organism is unclear and there is still uncertainty as to whether it is a protozoan or a fungus.

We have now found a novel class of 4-pyridone derivatives which exhibit activity against protozoa, in particular against the malarial parasite *Plasmodium falciparum*, and species of Eimeria as well as against the parasitic organism *Pneumocystis carinii*.

Thus, in a first aspect the present invention provides a compound of formula (I):

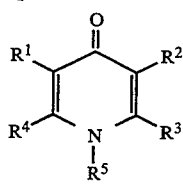

(I)

wherein $R^1$ represents a hydrogen or halogen atom, or a cyano group;

$R^2$ represents a carbocyclic group having 6 to 10 ring atoms and containing at least one aromatic ring; or a heterocyclic group having 5 to 10 ring atoms, including 1 to 4 heteroatoms selected from O, N and S, and containing at least one aromatic ring, said carbocyclic and heterocyclic groups being optionally substituted by a substituent selected from halogen, cyano, nitro, amino, mono-or di-$C_{1-4}$alkylamino, $C_{1-4}$alkyl, halo$C_{1-4}$alkyl, $C_{1-4}$alkoxy, $C_{1-4}$alkylsulphonyl, $C_{1-4}$alkylthio, $C_{1-6}$alkanoyl, pyridyl optionally substituted by halo$C_{1-4}$alkyl, pyridyloxy optionally substituted by halo$C_{1-4}$alkyl or the carbocyclic or heterocyclic group $R^2$ is optionally substituted by a group

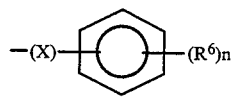

wherein

X represents —O—,

S(O)m, —CH$_2$O—, —OCH$_2$—, —CH$_2$S(O)m, —S(O)mCH$_2$—, —CYZ(CH$_2$)p or —(CH$_2$)pCYZ, or X is a single bond linking the phenyl groups;

Y and Z independently represent hydrogen, halogen or $C_{1-4}$alkyl;

$R^6$ represents halogen, cyano, nitro, amino, mono-or di-($C_{1-4}$)alkylamino, $C_{1-4}$alkyl, halo($C_{1-4}$)alkyl, $C_{1-4}$alkoxy or halo($C_{1-4}$)alkoxy, or S(O)$_m$$C_{1-4}$ alkyl;

n is zero or an integer from 1 to 5;

m is zero, one or two; and p is zero or one;

the carbocyclic or heterocyclic group $R^2$ being optionally further substituted by one or two substituents selected from halogen, cyano, nitro, amino, mono- or di-($C_{1-4}$)alkylamino, $C_{1-4}$alkyl, halo($C_{1-4}$)alkyl, $C_{1-4}$alkoxy and $C_{1-4}$alkylthio;

or $R^2$ represents a $C_{3-6}$cycloalkyl group or a $C_{3-6}$cycloalkyl-$C_{1-6}$alkyl group, wherein the cycloalkyl group or moiety is optionally substituted by $C_{1-6}$alkyl, $C_{3-6}$cycloalkyl or by a phenyl group which may itself be optionally substituted by $(R^6)$n as defined above;

or $R^2$ represents a $C_{1-10}$alkyl group, optionally substituted by hydroxy or $C_{1-6}$alkoxy, or by a carbocyclic or heterocyclic group as defined above;

$R^3$ and $R^4$, which may be the same or different, each represent a hydrogen or halogen atom, or a $C_{1-6}$alkyl group optionally substituted by 1 to 3 halogen atoms; and $R^5$ represents a hydrogen atom, a hydroxyl group, or a $C_{1-6}$alkyl group, optionally substituted by hydroxy, carboxy, amino or mono- or di-($C_{1-4}$)alkyl amino, and salts and other physiologically functional derivatives thereof.

In the above definitions, halogen includes fluorine, chlorine, bromine and iodine. Alkyl groups and moieties include straight and branched chains. A carbocyclic group may be for example phenyl, naphthyl or tetrahydronaphthyl. A heterocyclic group may be for example furyl, thienyl or pyridyl. Preferred substituents on an aromatic carbocyclic or heterocyclic group $R^2$ include phenyl, pyridyl, halogen, cyano, nitro, amino, mono- or di-($C_{1-4}$)alkyl-amino, $C_{1-4}$alkyl, halo-($C_{1-4}$)alkyl, $C_{1-4}$alkoxy, phenoxy, $C_{1-4}$ alkylsulphonyl, $C_{1-4}$alkylthio, $C_{1-6}$alkanoyl, phenylsulphonyl, phenylthio and benzoyl, wherein a phenyl group or moiety or a pyridyl group in the aforementioned substituents may itself be further optionally substituted by halogen, cyano, nitro, amino, mono- or di-($C_{1-4}$)alkylamino, $C_{1-4}$alkyl, halo-($C_{1-4}$)alkyl, $C_{1-4}$alkoxy, halo($C_{1-4}$)alkoxy, or —S(O)$_m$$C_{1-4}$alkyl, where m is zero, 1 or 2. A halo $C_{1-4}$ alkyl substituent present in the group $R^2$ preferably carries from one to three halogen atoms eg. fluorine, chlorine or bromine.

It will be appreciated that compounds of formula (I) wherein $R^5$ is hydrogen may exist in a tautomeric form, as a pyridinol of formula (IA)

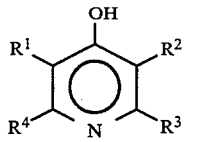
(IA)

and such tautomeric forms are included within the present invention.

Compounds of formula (I) which contain an acidic function may form salts with bases and compounds which contain a basic group (e.g. a basic amino group) may form salts with acids. Suitable base salts include inorganic base salts such as alkali metal (e.g. sodium and potassium) salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine. Suitable acid addition salts include those formed from hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic and glucuronic acids. Most preferably, the salts will be physiologically acceptable.

Physiologically functional derivatives of formula (I) are derivatives which are converted in vivo either by the host or the parasite into a compound of formula (I). Such derivatives include esters and ethers which may be formed for example with the tautomeric pyridinol form (IA). An ester may be formed for example with an alkanoic acid e.g. a $C_{1-6}$ alkanoic acid or with a phosphoric acid. Suitable ethers include $C_{1-6}$ alkyl ethers.

Thus, physiologically functional derivatives according to the invention include those of formula (IB):

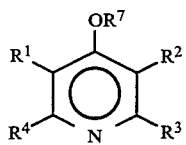
(IB)

wherein $R^1$, $R^2$, $R^3$ and $R^4$ are as hereinbefore defined and $R^7$ represents a $C_{1-6}$alkyl group; a group $OC(O)R^8$ wherein $R^8$ represents a $C_{1-6}$alkyl group; or a group $-OP(O)(OR^9)(OR^{10})$, wherein $R^9$ and $R^{10}$, which may be the same or different, each represent hydrogen or a $C_{1-6}$alkyl group. Preferably each of $R^7$, $R^8$, $R^9$ and $R^{10}$ represent a $C_{1-4}$alkyl group eg. methyl or ethyl.

In the compounds of formulae (I), (IA) and (IB)

$R^1$ is preferably a hydrogen atom or a halogen atom, such as chlorine or bromine. Most preferably $R^1$ is a halogen atom.

$R^2$ is preferably an optionally substituted $C_{3-6}$ cycloalkyl group, especially an optionally substituted cyclohexyl group, or an optionally substituted aromatic carbocyclic group as defined above, especially an optionally substituted phenyl group. A substituted $C_{3-6}$cycloalkyl group such as cyclohexyl is preferably substituted by a $C_{1-6}$alkyl group eg. t-butyl or by a phenyl group, which may be optionally substituted as defined above advantageously by halogen. Most preferably a cyclohexyl group $R^2$ is substituted at the 4-position with respect to the pyridone ring. A phenyl substituent is preferably substituted at the 3- or 4-position with respect to the cyclohexyl ring, advantageously by a halogen atom such as chlorine. When $R^2$ is a substituted aromatic carbocyclic group such as phenyl this is preferably substituted by one or two halogen atoms, or by a $C_{1-4}$alkoxy, halo $C_{1-4}$alkyl, phenyl, phenoxy, phenylsulphonyl, phenylthio, benzyl, α,α-difluorobenzyl, benzoyl or pyridyloxy group, wherein a phenyl or pyridyl group or moiety in the aforementioned substituents may itself be optionally substituted by one or two substituents selected from halo eg. fluoro, chloro or bromo; halo$C_{1-4}$alkyl eg. trifluoromethyl; $C_{1-4}$alkoxy eg. methoxy; halo $C_{1-4}$alkoxy eg. trifluoromethoxy; or $S(O)mC_{1-4}$alkyl wherein m is zero, 1 or 2 eg. methylthio, methylsulphinyl or methylsulphonyl.

$R^3$ and $R^4$ each preferably represent a $C_{1-6}$ alkyl group, especially a $C_{1-4}$ alkyl group such as methyl or ethyl.

$R^5$ is preferably a hydrogen atom.

A particularly preferred group of compounds within general formula (I) is that of formula (IC):

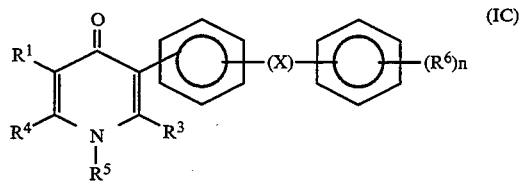
(IC)

wherein $R^1$ represents halogen eg. chlorine or bromine;

$R^3$ and $R^4$, which may be the same or different each represent a $C_{1-4}$ alkyl group;

$R^5$ represents a hydrogen atom;

X represents —O—,

S(O)m, —CH$_2$O—, —OCH$_2$—, —CH$_2$S(O)$\overline{m}$, —S(O)mCH$_2$—, —CYZ(CH$_2$)p or —(CH$_2$)pCYZ, or X is a single bond linking the phenyl groups;

Y and Z independently represent hydrogen, halogen or $C_{1-4}$ alkyl;

$R^6$ represents halogen, cyano, nitro, amino, mono- or di-($C_{1-4}$)alkylamino, $C_{1-4}$ alkyl, halo($C_{1-4}$)alkyl, $C_{1-4}$ alkoxy, halo($C_{1-4}$)alkoxy; or —S(O)m $C_{1-4}$ alkyl;

n is zero or an integer from 1 to 5 m is zero, one or two; and p is zero or one;

and physiologically acceptable salts and other physiologically functional derivatives thereof.

The group X may be linked to each of the phenyl rings at any unsubstituted position. Similarly the substituent(s) $R^6$ may be at any otherwise unsubstituted position of the phenyl ring. Preferably however X is attached to the 4-position with respect to the pyridone group and at least one $R^6$ is at the 3- or 4-position relative to X. Advantageously n is 1 or 2, most preferably 1.

X is preferably —O—, —S(O)m, —CYZ, or a single bond.

Most preferably $R^6$ represents a halogen atom (eg. chlorine), $CF_3$, or $OCF_3$ advantageously at the 3- or 4-position relative to X.

Physiologically functional derivatives of compounds (IC) are preferably $C_{1-6}$ alkyl ethers and $C_{1-6}$ alkyl and phosphate esters, as defined for formula (IB) hereinabove.

It will be understood that further references herein to compounds of formula (I) include compounds of formulae (IA), (IB) and (IC) unless otherwise indicated.

Specific compounds within the scope of formula (I) include:

3-(4-(4-Chlorophenoxy)phenyl)-2,6-dimethylpyridin-4(1H)-one
3-[4-(4-Trifluoromethylphenoxy)phenyl]-2,6-dimethyl-pyridin-4(1H)-one
3-(4'-Chloro-4-biphenylyl)-2,6-dimethylpyridin-4(1H)-one
3-Bromo-5-(4'-chloro-4-biphenylyl)-2,6-dimethylpyridin-4(1H)-one
3-Chloro-5-(4'-chloro-4-biphenylyl)-2,6-dimethylpyridin-4(1H)-one
5-Iodo-2,6-dimethyl-3-octylpyridin-4(1H)-one
5-Cyano-2,6-dimethyl-3-octylpyridin-4(1H)-one
3-(4-Chlorophenyl)-1,2,6-trimethylpyridin-4-one
3-Bromo-5-(4-chlorophenyl)-1,2,6-trimethylpyridin-4-one
3-(4-(4-trifluoromethoxyphenoxy)phenyl)-2,6-dimethylpyridin-4-(1H)-one
3-Bromo-2,6-dimethyl-5-(4-(4-methylsulphinylphenoxy)phenyl)pyridin-4(1H)-one
3-Bromo-2,6-dimethyl-5-phenylpyridin-4(1H)-one
3-Chloro-2,6-dimethyl-5-phenylpyridin-4(1H)-one
2,6-Dimethyl-3-(4-chlorophenyl)-pyridin-4(1H)-one
3-Bromo-5-(4-chlorophenyl)-2,6-dimethylpyridin-4(1H)-one
3-Chloro-5-(4-chlorophenyl)-2,6-dimethylpyridin-4(1H)-one
3-Bromo-5-(4-fluorophenyl)-2,6-dimethylpyridin-4(1H)-one
3-Chloro-5-(4-fluorophenyl)-2,6-dimethylpyridin-4(1H)-one
3-Bromo-2,6-dimethyl-5-[4-(trifluoromethyl)phenyl]-pyridin-4(1H)-one
5-(3,4-Dichlorophenyl)-2,6-dimethylpyridin-4(1H)-one
3-Bromo-5-(3,4-dichlorophenyl)-2,6-dimethylpyridin-4(1H)-one
3-Chloro-5-(3,4-dichlorophenyl)-2,6-dimethylpyridin-4(1H)-one
3-(2,4-Dichlorophenyl)-2,6-dimethylpyridin-4(1H)-one
3-Bromo-5-(2,4-dichlorophenyl)-2,6-dimethyl-pyridin-4(1H)-one
3-Bromo-5-(4-methoxyphenyl)-2,6-dimethylpyridin-4(1H)-one
3-(4-Biphenylyl)-2,6-dimethylpyridin-4(1H)-one
3-(4-Biphenylyl)-5-bromo-2,6-dimethylpyridin-4(1H)-one
3-(4'-Fluoro-4-biphenylyl)-2,6-dimethylpyridin-4(1H)-one
3-Bromo-5-(4'-fluoro-4-biphenylyl)-2,6-dimethylpyridin-4(1H)-one
3-Chloro-5-(4'-fluoro-4-biphenylyl)-2,6-dimethylpyridin-4(1H)-one
2,6-Dimethyl-3-(4-phenoxyphenyl)pyridin-4(1H)-one
3-Bromo-5-(4-phenoxyphenyl)-2,6-dimethylpyridin-4(1H)-one
3-Bromo-5-[4-(4-fluorophenoxy)phenyl]-2,6-dimethylpyridin-4(1H)-one
2,6-Dimethyl-3-[4-(3-trifluoromethylphenoxy)phenyl]-pyridin-4(1H)-one
-[4-(4-Chlorophenylthio)phenyl]-2,6-dimethylpyridin-4(1H)-one
3-Bromo-5-[4-(4-chlorophenylthio)phenyl]-2,6-dimethylpyridin-4(1H)-one
3-[4-(4-Chlorophenylsulphonyl)phenyl]-2,6-dimethyl-pyridin-4(1H)-one
3-Bromo-5-[4-(4-chlorophenylsulphonyl)phenyl]-2,6-dimethylpyridin-4(1H)-one
3-Chloro-5-[4-(4-chlorophenylsulphonyl)phenyl[-2,6-dimethylpyridin-4(1H)-one
3-(3-(4-Chlorophenoxy)phenyl)-2,6-dimethylpyridin-4(1H)-one
3-Bromo-5-[3-(4-chlorophenoxy)phenyl]-2,6-dimethyl-pyridin-4(1H)-one
3-Bromo-5-(3-chloro-4-(4-chlorophenoxy)phenyl)-2,6-dimethylpyridin-4(1H)-one
3-Bromo-5-[4-(4-chlorobenzoyl)phenyl]-2,6-dimethyl-pyridin-4(1H)-one
3-Chloro-5-[4-(4-chlorobenzoyl)phenyl]-2,6-dimethyl-pyridin-4(1H)-one
2,6-dimethyl-3-octylpyridin-4(1H)-one
3-Bromo-2,6-dimethyl-5-octylpyridin-4(1H)-one
3-Chloro-2,6-dimethyl-5-octylpyridin-4(1H)-one
3-Cyclohexyl-2,6-dimethylpyridin-4(1H)-one
3-Bromo-5-cyclohexyl-2,6-dimethylpyridin-4(1H)-one
3-Cyclohexylmethyl-2,6-dimethylpyridin-4(1H)-one
3-Bromo-2,6-dimethyl-5-cyclohexylmethylpyridin-4(1H)-one
Trans-2,6-dimethyl-3-(4-t-butylcyclohexyl)pyridin-4(1H)-one
trans-3-Bromo-2,6-dimethyl-5-(4-t-butylcyclohexyl)-pyridin-4(1H)-one
3-[trans-4-(4-Chlorphenyl)cyclohexyl]-2,6-dimethyl-pyridin-4(1H)-one
3-Bromo-5-[trans-4-(4-chlorophenyl)cyclohexyl]-2,6-dimethylpyridin-4(1H)-one
trans-3-Chloro-5-[4-(4-chlorophenyl)cyclohexyl]-2,6-dimethylpyridin-4(1H)-one
3-(trans-4-(4-chlorophenyl)cyclohexylmethyl-2,6-dimethylpyridin-4(1H)-one
3-Bromo-1,2,6-trimethyl-5-octylpyridin-4-one
3-[trans-4-(4-Chlorophenyl)cyclohexyl)-1,2,6-trimethylpyridin-4-one
3-(4-(3-Trifluoromethoxyphenoxy)phenyl)-2,6-dimethylpyridin-4(1H)-one
3-Bromo-5-(4-(3-trifluoromethoxyphenoxy)phenyl)-2,6-dimethylpyridin-4(1H)-one
3-Chloro-5-(4-(3-trifluoromethoxyphenoxy)phenyl)-2,6-dimethylpyridin-4(1H)-one
3-Bromo-2,6-dimethyl-4-methoxy-5-[4-(4-trifluoromethoxyphenoxy)phenyl]pyridine
4-Acetoxy-3-chloro-2,6-dimethyl-5-[4-(4-trifluoromethoxyphenoxy)phenyl]pyridine
3-(4-(4-Chlorophenoxy)phenyl)-1-hydroxy-2,6-dimethylpyridin-4-one
3-Bromo-5-(4-(4-chlorophenoxy)phenyl)-1-hydroxy-2,6-dimethylpyridin-4-one
3-Bromo-2,6-dimethyl-5-[4-(4-trifluoromethoxyphenoxy)phenyl]-4-pyridinyl diethyl phosphate Particularly preferred compounds of formula (I) include:

3-Bromo-5-[4-(4-chlorophenoxy)phenyl]-2,6-dimethyl-pyridin-4(1H)-one

3-Chloro-5-[4-(4-chlorophenoxy)phenyl]-2,6-dimethyl-
pyridin-4(1H)-one
3-Bromo-5-[4-(4-trifluoromethylphenoxy)phenyl]-2,6-
dimethylpyridin-4(1H)-one
3-Bromo-5-(4-(4-trifluromethoxyphenoxy)phenyl)-2,6-
dimethylpyridin-4(1H)-one
3-chloro-5-(4-(4-trifluoromethoxyphenoxy)phenyl)-2,6-
dimethylpyridin-4(1H)-one
3-Bromo-2,6-dimethyl-5-[4-(3-trifluoromethylphenox-
y)phenyl]pyridin-4(1H)-one
3-chloro-2,6-dimethyl-5-[4-(3-trifluoromethylphenoxy)-
phenyl]pyridin-4(1H)-one
3-chloro-2,6-dimethyl-5-[4-(3-trifluoromethoxyphenox-
y)phenyl]pyridin-4(1H)one
3-bromo-2,6-dimethyl-5-[4-(3-trifluoromethoxyphenox-
y)phenyl]pyridin-4(1H)-one
4-acetoxy-3-chloro-2,6-dimethyl-5-[4-(4-trifluorome-
thoxyphenoxy)phenyl]pyridine; and
3-chloro-5-[4-(4-trifluoromethylphenoxy)phenyl]-2,6-
dimethylpyridin-4(1H)-one.

Compounds of formula (I) have been found to exhibit good activity in vitro against the human malaria parasite *Plasmodium falciparum*, and also demonstrate good activity in experimental infections with *Plasmodium voelii* in mice. Compounds of formula (I) have also been found to exhibit activity in vivo in chicks infected with *Eimeria tenella* and *Eimeria maxima*, which are both causitive organisms of coccidiosis. In addition activity has been demonstrated against an experimental *P.carinii* infection in rats. The compounds are thus useful for the treatment and/or prophylaxis of parasitic infections, such as those caused by parasitic protozoa e.g. malaria and those caused by *P.carinii*, in mammals, including humans.

It will be appreciated that the amount of the compound of formula (I) or its salt or other physiologically functional derivative required for use in the treatment or prophylaxis of parasitic infections will depend inter alia on the route of administration, the age and weight of the mammal (e.g. human) to be treated and the nature and severity of the condition being treated. In general, a suitable dose for administration to man is in the range of 0.1 mg to 200 mg per kilogram bodyweight per day, for example from 1 mg/kg to 100 mg/kg, particularly 10 to 40 mg/kg. It will be appreciated that for administration to neonates, lower doses may be required.

For prophylactic treatment the compound of formula (I) or its salt or other physiologically functional derivative may also be given less frequently, e.g. as a single dose on alternate days, once or twice per week or once or twice per month. The dosage for prophylatic treatment will depend inter alia on the frequency of administration, and, where a depot preparation or controlled release formulation is used the rate of release of the active ingredient. Thus for once-weekly administration a suitable prophylactic dose is in the range 0.1 to 100 mg/kg, e.g. 0.5 to 50 mg/kg particularly 5 to 50 mg/kg.

It should be understood that the dosages referred to above are calculated in terms of the compound of formula (I) per se.

The present invention thus further provides a method for the treatment and/or prophylaxis of parasitic infections e.g. parasitic protozoal infections such as malaria or coccidiosis, or infections caused by *P.carinii*, in mammals e.g. humans, which comprises administering to a mammal suffering from or susceptible to said infection, with an effective amount of a compound of formula (I) or a physiologically acceptable salt or other physiologically functional derivative thereof.

There is also provided a compound of formula (I) or a physiologically acceptable salt or other physiologically functional derivative thereof for use in therapy, e.g. in the treatment and/or prophylaxis of parasitic diseases as hereinbefore defined.

The invention also provides the use of a compound of formula (I) or a physiologically acceptable salt or other physiologically functional derivative thereof for the manufacture of a medicament for the treatment and/or prophylaxis of parasitic infections as hereinbefore defined.

For use according to the present invention a compound of formula (I) or a physiologically acceptable salt or other physiologically functional derivative thereof is preferably presented as a therapeutic (ie. pharmaceutical or veterinary) formulation.

Therapeutic formulations comprise an active ingredient (that is, a compound of formula (I) or a physiologically acceptable salt or other physiologically functional derivative thereof) together with one or more pharmaceutically or veterinarily acceptable carriers therefor and optionally other therapeutic and/or prophylactic ingredients. The carrier(s) must be acceptable in the sense of being compatible with the other ingredients of the formula and not deleterious to the recipient thereof.

The present invention, therefore, further provides a therapeutic formulation comprising a compound of formula (I) or a physiologically acceptable salt or physiologically functional derivative thereof together with a pharmaceutically or veterinarily acceptable carrier therefor.

There is also provided a method for the preparation of a therapeutic formulation comprising bringing into association a compound of formula (I) or a physiologically acceptable salt or physiologically functional derivative thereof, and a pharmaceutically or veterinarily acceptable carrier therefor.

The compound of formula (I) or its salt or other physiologically functional derivative may conveniently be presented as a therapeutic formulation in unit dosage form. A convenient unit dose formulation contains the active ingredient in an amount of from 10 mg to 1 g.

Therapeutic formulations include those suitable for oral, topical (including dermal, buccal and sublingual), rectal and parenteral (including subcutaneous, intradermal, intramuscular and intravenous) administration. The formulation may, where appropriate, be conveniently presented in discrete dosage units and may be prepared by any of the methods well known in the art of pharmacy. All methods include the step of bringing into association the compound of formula (I) or a physiologically acceptable salt or other physiologically functional derivative thereof with liquid carriers or finely divided solid carriers or both and then, if necessary, shaping the product into the desired formulation.

Therapeutic formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active ingredient in a free-flowing form such as a powder or granules optionally mixed with a binder, lubricant, inert diluent, lubricating agent, surface-active agent or dispersing agent. Moulded tablets may be made by moulding an active ingredient with an inert liquid diluent. Tablets may be optionally coated and, if uncoated, may optionally be scored. Capsules may be prepared by filling the active ingredient, either alone or in admixture with one or more accessory ingredients, into the capsule shells and then sealing them in the usual manner. Cachets are analogous to capsules wherein the active ingredient together with any accessory ingredient(s) is sealed in a rice paper envelope. A compound of formula (I) or a physiologically acceptable salt or other physiologically functional derivative thereof may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredient is formulated in an appropriate release—controlling matrix, or is coated with a suitable release—controlling film. Such formulations may be particularly convenient for prophylactic use.

Therapeutic formulations suitable for rectal administration wherein the carrier is a solid are most preferably presented as unit dose suppositories. Suitable carriers include cocoa butter and other materials commonly used in the art. The suppositories may be conveniently formed by admixture of the active ingredient with the softened or melted carrier(s) followed by chilling and shaping in moulds.

Therapeutic formulations suitable for parenteral administration include sterile solutions or suspensions of the active ingredient in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compound of formula (I) or a physiologically acceptable salt or other physiologically functional derivative thereof may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the therapeutic formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The compounds of the present invention may be administered in combination or concurrently with other therapeutic agents, for example other antimalarial agents, such as chloroquine, mefloquine, quinine, artemesinin, halofantrine, pyrimethamine, or hydroxynaphthoquinones such as those described in European Patent Application No. 123238; anticoccidial agents such as monensin, halofuginone, arprinocid, amprolium, dinitolmide, robenidine or salinomycin; or antibiotics such as clindamycin, tetracycline or doxycycline. In particular, compounds of formula (I) have been found to potentiate the activity of hydroxynaphthoquinones eg. those described in European Patent Application No. 123238, such as 2-[4-(4-Chlorophenyl)cyclohexyl-3-hydroxy-1,4-naphthoquinone, against *P.falciparum* and *P.carinii.* In a further aspect therefore, the present invention provides synergistic compositions comprising a compound of formula (I) and a hydroxynaphthoquinone.

When compounds of formula (I) are used in combination with a second therapeutic agent the dose of each compound will vary from that required when the compound is used alone. Appropriate dosages can be readily determined by those skilled in the art.

Formulations suitable for veterinary use include those adapted for oral, parenteral, and intrarumenal administration.

Veterinary formulations suitable for oral administration include drenches (oral liquid dosing), which may be solutions or suspensions; tablets, boluses, pastes, or in-feed preparations in the form of powders, granules or pellets.

Alternatively, veterinary formulations may be adapted to be administered parenterally by sub-cutaneous, intramuscular or intravenous injection of a sterile solution or suspension, by implantation or as an intramammary injection whereby a suspension or solution is introduced into the udder via the teat.

For intrarumenal injection, the compounds of the invention may be formulated as solutions or solid or micocapusule suspensions. Typically the formulations are similar to the oral liquid preparations or parenteral preparations described herein. Such formulations are injected directly into the rumen, usually through the side of the animal, for example by a hypodermic syringe and needle or by an automatic injection device capable of giving single or multiple doses.

For veterinary administration a compound of formula (I) or its salt or other physiologically functional derivative is preferably formulated with one or more veterinarily acceptable carriers.

For oral administration, fine powders or granules may contain diluting agents, for example lactose, calcium carbonate, calcium phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethylcellulose, guar based vegetable gums, sodium alginates or sodium starch glycolates; granulating or binding agents such as starch in the form of mucilage, starch derivatives, such as "Snow Flake", cellulose derivatives such as talc, calcium stearate, methyl cellulose, gelatin or polyvinylpyrrolidone; and/or lubricating agents, such as magnesium stearate or stearic acid.

For parenteral administration, the compounds may be presented in sterile injection solutions which may contain antioxidants or buffers, or as injectable suspensions. Suitable solvents include water, in the case of suspensions, and organic solvents such as dimethylformamide, dimethylacetamide, diethylacetamide, ethyl lactate, ethyl akate, dimethylsulphoxide, alcohols, e.g. ethanol, glycols, e.g. ethylene glycol, propylene glycol, butylene glycol and hexamethylene glycol, polyethylene glycols containing 2 to 159 ethylene glycol monomer units and having average molecular weights from about 90 to 7500, glycerin formal, glycofural, glyerol, isopropylmyristate N-methylpyrrolidone, 2-pyrrolidone polyethylene glycoethers of tetrahydrofurfuryl alcohol and diethylene glycol, and fixed and neutral oils, for example fractionated coconut oil. Parenteral formulations may also contain isotonic agents.

For veterinary use a compound of formula (I) may be employed together with other therapeutic agents used in the field of animal health, for example with anticoccidial and/or antitheilerial agents According to a further aspect of the present invention there is also provided a process for the preparation of compounds of formula (I) and physiologically acceptable salts and other physiologically functional derivatives thereof, which comprises (A) to prepare a compound of formula (I) wherein $R^1$ represents a hydrogen atom the reaction of a compound of formula (II)

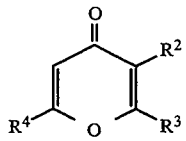
(II)

with ammonia or a derivative thereof.

(B) to prepare a compound of formula (I) wherein $R^1$ is a halogen atom, the reaction of a compound of formula (I) wherein $R^1$ is hydrogen with a halogenating agent;

(C) to prepare a compound of formula (I) wherein $R^1$ is a cyano group, the reaction of a compound of formula (I) wherein $R^1$ is iodine, with a metal nitrile;

(D) to prepare a compound of formula (IB), the reaction of a compound of formula (I) with an alkylating, acylating or phosphorylating agent.

Process (A) may be effected using a compound $H_2NR^5$. Thus, for example aqueous ammonia may be used to prepare a compound wherein $R^5$ is hydrogen. To prepare a compound where $R^5$ is other than hydrogen, the appropriate optionally substituted alkylamine derivative may be employed eg. methylamine or hydroxylamine. The reaction may be conveniently carried out at a temperature in the range of 20° to 175° C. The reaction may be effected in a water miscible organic solvent, for example an alcohol such as ethanol.

Halogenating agents which may be employed in process (B) include N-halosuccinimide e.g. N-chloro- or N-bromo-succinimide, bromine, phosphorus pentachloride, thionyl chloride or bromide or oxalyl chloride. Solvents which may be employed include acetic acid, water and halogenated solvents eg. dichloromethane.

The reaction may conveniently be effected at a temperature in the range 0° to 100° C.

A preferred metal nitrile for use in Process (C) is cuprous cyanide. The reaction may be effected in a polar solvent, such as N,N-dimethylformamide or an alcohol. Conveniently the reaction temperature is in the range 15° to 200° C.

Alkylation according to Process (D) may be effected by methods well known in the art, using for example an alkylating agent such as the corresponding alkyl halide or dialkylsulphate, eg. methyl iodide or dimethylsulphate. The alkylation is conveniently carried out in the presence of a base, to generate the required pyridinol carbanion. Bases which may be employed include alkali metal and alkaline earth metal carbonates and alkoxides eg. potassium carbonate or potassium t-butoxide. Acylation or phosphorylation may be effected using the appropriate acid or a corresponding acylating or phosphorylating agent. Acylating agents which may be employed include acid halides eg. acid chlorides, eg. acetyl chloride; acid anhydrides; and activated esters. Phosphorylating agents include phosphorus oxyhalides; phosphoric acid esters eg. a mono-, di-or tri-($C_{1-6}$ alkyl) phosphate such as diethylchlorophosphate; and phosphoric acid anhydrides. Alkylation, acylation and phosphorylation may conveniently be effected in the presence of a solvent such as dimethylformamide, and at a non-extreme temperature, for example in the range 0° to 100° C.

The compounds of formula (II) may be prepared by reaction of a compound of formula (III):

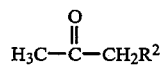
(III)

with an acid anhydride of formula (IV)

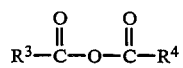
(IV)

The compound (IV) may be a mixed anhydride, or, where $R^3$ and $R^4$ are the same, a symmetrical anhydride. Alternatively, to prepare compounds wherein $R^3$ and $R^4$ are the same, the corresponding acid may be used. The reaction is advantageously carried out in the presence of polyphosporic acid, and at elevated temperature, e.g. in the range 50° to 120° C.

Compounds of formula (III) may be prepared by various methods known in the art for preparing analogous compounds, which methods include:

(i) reduction of the corresponding nitropropene derivative of formula (V):

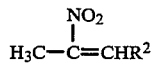
(V)

for example using the method described by F. A. Ramirez and A. Burger (*J. Am. Chem. Soc.* vol 72, 2781, 1950);

(ii) to prepare compounds of formula (III) wherein $R^2$ is an aryl group, reaction with potassium acetylacetonate in the presence of cuprous iodide, followed by deacetylation of the initial β-diketone product under alkaline conditions, according to the following reaction scheme:

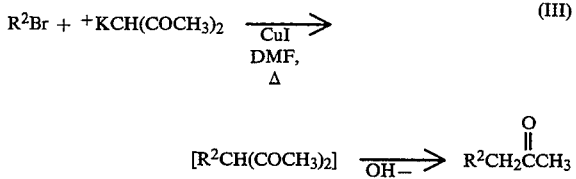

(see S. Sugai, et al., *Chem Letts*, 597 1982)

(iii) the palladium—catalysed coupling of a tin enolate, generated in situ from isopropenyl acetate and tri-n-butyltin methoxide, as shown in the following scheme:

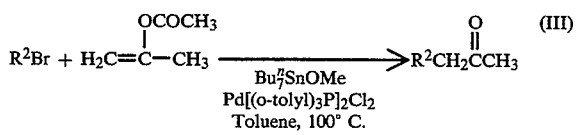

(see M. Kosugi et al, *Bull Chem Soc. Japan*, vol 57,242, 1984).

(iv) Reaction of the corresponding carboxylic acid $R^2CH_2COOH$ with lithium hydride, followed by methyl lithium; and (v) Reaction of the bromide $R^2CH_2Br$ with magnesium to form a Grignard reagent which is then reacted with acetic anhydride to form a compound of formula (III).

Compounds of formula (V) may themselves be prepared by reaction of the corresponding aldehyde of formula (VI):

with nitroethane.

The invention will now be illustrated by the following non-limiting examples.

The following abbreviations are used in the preparations and examples:
DMF—N,N-dimethylformamide.
DMSO—dimethylsulphoxide.
DME—1,2-dimethoxyethane.
All temperatures are in degrees Celsius (°C.).

PREPARATION OF INTERMEDIATES

Preparation 1

4-(4-Chlorophenoxy)benzaldehyde

4-Chlorophenol (22.6 g) was added to a stirred solution of sodium methoxide (9.5 g) in methanol (80 ml). After 30 min the solvent was evaporated in vacuo. Residual traces of methanol were removed by addition of toluene and evaporating again in vacuo. The residue was taken up in DMF (200 ml) and 4-fluorobenzaldehyde (19.85 g) added. The mixture was stirred and heated at 120° for 4 hr, cooled, poured into water and extracted with toluene (2×200 ml). The combined extracts were washed with water, 2M sodium hydroxide and satd. brine, dried over magnesium sulphate and concentrated to leave a brown oil. Distillation gave the title compound (26.03 g), b.p.=140°–50°/0.5 mm.

The following compounds were prepared from the appropriate phenols by the general procedure described for preparation 1:
(a) 4-(3-Chlorophenoxy)benzaldehyde.
(b) 4-(3-Trifluoromethylphenoxy)benzaldehyde.
(c) 4-(4-Fluorophenoxy)benzaldehyde, m.p. 74°–77°.
(d) 4-(4-Methoxyphenoxy)benzaldehyde, m.p. 48°–50°.
(e) 4-(4-Methylthiophenoxy)benzaldehyde.
(f) 4-(3,4-Dichlorophenoxy)benzaldehyde.
(g) 4-(3,5-Dichlorophenoxy)benzaldehyde.
(h) 4-(2,4-Dichlorophenoxy)benzaldehyde.
(i) 4-(4-Chlorophenylthio)benzaldehyde, m.p. 82°–84°.
(j) 4-(4-Trifluoromethoxyphenoxy)benzaldehyde, b.p. 130°–135°/0.5 mm, NMR δH (CDCl$_3$) 9.86 (1H, s), 8.0–7.7 (2H, m), 7.5–6.9 (6H, m).
(k) 4-(3-Trifluoromethoxyphenoxy)benzaldehyde. NMR δH (CDCl$_3$) 9.9(1H,S); 7.95–7.75 (2H,m); 7.4–6.9 (6H,m).

Preparation 2

4-(4-Chlorophenoxy)phenylpropan-2-one

A mixture of 4-(4-chlorophenoxy)benzaldehyde (256 g) and butylamine (239 ml) in toluene (1 liter) was heated to reflux and the water formed removed through a Dean & Stark head. After 2 hr the mixture was concentrated in vacuo and the residue dissolved in acetic acid (750 ml) and nitroethane (118.5 ml), heated at 100° for 2 hr, cooled and poured into iced water. The yellow solid was filtered, dried in air and recyrstallised from ethanol (750 ml) to afford 4-(4-chlorophenoxy)phenyl-2-nitropropene (254.7 g), m.p. 69°–71°. Acetic acid (115 ml) was added over 30 min to a well stirred, refluxing mixture of the 4-(4-chlorophenoxy)phenyl-2-nitropropene (28.9 g), iron powder (56 g), water (20 ml) and methanol (150 ml). After 3 hr it was cooled and partitioned between water (500 ml) and dichloromethane (200 ml). The organic phase was filtered, washed with water and satd. aq. sodium bicarbonate, dried over magnesium sulphate and concentrated in vacuo to leave a yellow oil. Trituration with hexane afforded the title compound as fine colourless crystals (14.6 g), m.p. 50°–52°.

The following compounds were prepared from the appropriate aldehyde by the general procedure described for preparation 2:
(a) 4-(3-Chlorophenoxy)phenylpropan-2-one, NMR δH (CDCl$_3$) 7.45–6.6 (8H, m), 3.6 (2H, s), 2.1 (3H, s).
(b) 4-(3-Trifluoromethylphenoxy)phenylpropan-2-one, NMR δH (CDCl$_3$) 7.4–6.7 (8H, m), 3.6 (2H, s), 2.1 (3H, s).
(c) 4-(4-Fluorophenoxy)phenylpropan-2-one, m.p. 51°–54°, NMR δH (CDCl$_3$) 7.3–6.7 (7H, m), 3.64 (2H, s), 2.15 (3H, s).
(d) 4-(4-Methoxyphenoxy)phenylpropan-2-one, NMR δH (CDCl$_3$) 7.3–6.6 (7H, m),3.7 (3H, s), 3.6 (2H, s), 2.1 (3H, s).
(e) 4-(4-Methylthiophenoxy)phenylpropan-2-one, NMR δH (CDCl$_3$) 7.4–6.7 (8H, m), 3.64 (2H, s), 2.45 (3H, s), 2.15 (3H, s).
(f) 4-(3,4-Dichlorophenoxy)phenylpropan-2-one, m.p. 78°–80°, NMR δH (CDCl$_3$) 7.4–6.65 (7H, m), 3.65 (2H, s), 2.1 (3H, s).
(g) 4-(3,5-Dichlorophenoxy)phenylpropan-2-one.
(h) 4-(2,4-Dichlorophenoxy)phenylpropan-2-one, NMR δH (CDCl$_3$) 7.3–6.3 (7H, m), 3.55 (2H, s), 2.1 (3H, s).
(i) 4-(4-Chlorophenylthio)phenylpropan-2-one.
(j) 4-(4-Trifluoromethoxyphenoxy)phenylpropan-2-one, m.p. 57°–58°, NMR δH (CDCl$_3$) 7.4–6.85 (8H, m), 3.7 (2H, s), 2.2 (3H, s).
(k) 4-(3-Trifluoromethoxyphenoxy)phenylpropan-2-one NMR δH (CDCl$_3$) 7.3–6.7 (8H,m); 3.6(2H,s); 2.1(3H,s).

Preparation 3

4-(4-Chlorophenyl)phenylpropan-2-one

To a stirred solution of 4-bromo-4'-chlorobiphenyl (16 g; F. R. Shaw and E. E. Turner. *J. Chem. Soc.*, 285 (1932) ), isopropenyl acetate (9 g) and dichlorobis(tri-o-tolylphosphine)palladium (0.47 g) in dry toluene (30 ml), under nitrogen, was added tributyltin methoxide (25.9 ml; Aldrich). The mixture was stirred and heated at 100° for 5 hr, cooled and the solvent evaporated in vacuo. The residue was chromatographed on silica gel, eluting with cyclohexane then ether. The resultant solid was recrystallised from cyclohexane to afford the title compound (10 g), m.p. 79°–81°.

The following compounds were prepared from the appropriate bromo derivatives by the general procedure described for preparation 3:

(a) 4-Biphenylylpropan-2-one, NMR δH (CDCl$_3$) 7.7–7 (9H, m), 3.65 (2H, s), 2.1 (3H, s). (From 4-bromobiphenyl—Aldrich).

(b) 4'-Fluoro-4-biphenylylpropan-2-one, m.p. 68°–70°, NMR δH (CDCl$_3$) 7.8–7.7.0 (8H, m), 3.76 (2H, s), 2.2 (3H, s). (From 4-bromo-4'-fluorobiphenyl prepared by the bromination of 4'-fluorobiphenyl following the procedure of F. R. Shaw and E. E. Turner, J. Chem. Soc., 285, 1932).

(c) 3-(4-Chlorophenoxy)phenylpropan-2-one.

(d) 4-(5-Trifluormethylpyrid-2-yloxy)phenylpropan-2-one, m.p. 58°–61°, NMR δH (CDCl$_3$). (From 2-(4-bromophenoxy)-5-trifluoromethylpyridine, prepared by the reaction of the sodium salt of 4-bromophenol with 2-chloro-5-trifluoromethylpyridine).

(e) 4-(4-Chlorophenylsulphonyl)phenylpropan-2-one, NMR δH (CDCl$_3$) 8.1–7.1 (8H, m), 3.72 (2H, s), 2.1 (3H, s). (From 4-bromo-4'-chlorodiphenylsulphone, L. G. Groves and E. E. Turner, J. Chem. Soc., 509, 1928).

(f) 4-(4-Chlorophenacyl)phenylpropan-2-one, m.p. 98°–100°. (From 4-bromo-4'-chlorobenzophenone, L. G. Groves and E. E. Turner, J. Chem. Soc., 509, 1928).

(g) 4-(4-Chlorobenzyl)phenylpropan-2-one, NMR δH (CDCl$_3$) 7.3–6.8 (8H, m), 3.76 (2H, s), 3.5 (2H, s), 1.98 (3H, s). (From 4-bromo-(4-chlorophenyl)methylbenzene, m.p. 58°–59°, prepared by the reduction of 4-bromo-4'-chlorobenzophenone with sodium borohydride in trifluoroacetic acid, following the procedure of G. W. Gribble, W. J. Kelly and S. E. Emery, Synthesis, 763, 1978).

(h) 4-(4-Chlorodifluorobenzyl)phenylpropan-2-one, m.p. 90°–93°, NMR δH (CDCl$_3$) 7.8–6.85 (8H, m), 3.75 (2H, s), 2.15 (3H, s). From 4-bromo-(4-chlorophenyl)difluoromethylbenzene, m.p. 55°–57°. (Prepared from 4-bromo-4'-chlorobenzophenone following the procedure of H. Volz and W. D. Mayer, Ann. Chem., 1407, 1981).

(i) 3-Chloro-4-(4-chlorophenoxy)phenylpropan-2-one, NMR δH (CDCl$_3$) 7.5–6.8 (7H, m), 3.7 (2H, s), 2.24 (3H, s). (From 4-bromo-2,4'-dichlorodiphenyl ether prepared from 4-amino-2,4'-dichlorodiphenyl ether).

Preparation 4

4-bromo-4'-trifluoromethyldiphenylether

To a solution of 4-bromophenol (86.5 g) in DMSO (1.25 liters) was added potassium t-butoxide (56 g) and 4-chlorobenzotrifluoride (90 g; Aldrich). The mixture was stirred and heated at 160° for 3 days, cooled, poured into iced water and extracted with toluene (3×400 ml). The combined extracts were washed with 2N sodium hydroxide and water, dried over magnesium sulphate and concentrated to leave an oil. Distillation afforded the title compound (133.6 g), b.p.=94°–96°/0.15 mm.

Preparation 5

4-(4-Trifluoromethylphenoxy)phenylpropan-2-one

To a stirred solution of 4-bromo-4'-trifluoromethyldiphenylether (53.9 g) in DMF (1 liter) was added cuprous iodide (32.4 g) and potassium acetylacetonate hemihydrate (125 g; Aldrich). The mixture was stirred and heated at 100° for 24 hr, cooled, stirred with 2M sodium hydroxide (250 ml) for 1 hr and extracted with toluene (2×500 ml). The combined extracts were washed with water, 1M hdrochloric acid and satd. aq. sodium bicarbonate, dried over magnesium sulphate and concentrated in vacuo to leave a dark brown oil. Trituration with 1:1 ether/hexane followed by recrystallisation from hexane afforded the title compound as colourless crystals (32.1 g), m.p. 88°–90°, Nmr δH (CDCl$_3$) 6.5–7.8 (8H, m), 3.62 (2H, s), 2.18 (3H, s).

Preparation 6 trans-( 4-t-Butylcyclohexyl)propan-2-one

A solution of trans-(4-t-butylcyclohexyl)acetic acid (9.96 g) in dry DME (30 ml) was added over 10 min to a vigorously stirred suspension of powdered lithium hydride (0.5 g) in dry DME (30 ml). The mixture was refluxed for 2.5 hr, cooled on ice and a solution of methyl lithium in ether (63 ml; 1.6M solution) added over 30 min. The mixture was then stirred at room temperature for 2 hr, and poured into a mixture of conc. hydrochloric acid (13.5 ml) and water (200 ml). The organic phase was separated and the residue extracted with ether. The extracts were combined, washed with aq. sodium carbonate and satd. brine, dried over magnesium sulphate and concentrated in vacuo. Distillation afforded the title compound (7.7 g), b.p. 90°–100°/0.3 mm, NMR δH (CDCl$_3$) 2.28 (2H, d, J 7Hz), 2.12 (3H, s), 1.85–1.65 (6H, m), 1.05–0.85 (4H, m), 0.85 (9H, s).

Preparation 7 trans-(4-(4-Chlorophenyl)cyclohexyl)propan-2-one

To a stirred suspension of trans-(4-(4-chlorophenyl)cyclohexane)carboxylic acid (47.74 g) in dry ether (250 ml), under nitrogen, was added dropwise borane-methyl sulphide complex (8 ml; ca.10M solution—Aldrich). After 30 min the mixture was heated to reflux and further borane-methyl sulphide complex (16 ml) added. After 1 hr the mixture was cooled to room temperature and poured into methanol (500 ml). The solvent was evaporated in vacuo and the residue treated again with methanol (100 ml) followed by concentration in vacuo, to give trans-(4-(4-chlorophenyl)cyclohexyl) methanol (44 g), m.p. 60°–63°. A portion of this alcohol (41 g) was added to 48% hydrobromic acid (61 g) and conc. sulphuric acid (20 g). The mixture was stirred and heated at 140° for 5.5 hr, cooled and poured into iced water. The precipitate was filtered, dissolved in ether, washed with satd. aq. sodium bicarbonate and brine, dried over magnesium sulphate and the solvent evaporated in vacuo to leave a brown oil. Trituration with cold hexane gave trans-(4-(4-chlorophenyl)cyclohexyl)methyl bromide (44 g), m.p. 36°–38°. To magnesium turnings (33.06 g) in dry ether (70 ml) under nitrogen was added a crystal of iodine followed by a solution of the bromide (19.7 g) in ether (20 ml). The mixture was heated at reflux for a further 30 min, cooled to room temperature and then added dropwise to vigorously stirred acetic anhydride in dry ether (70 ml) at −78°, such that the temperature did not exceed −70°. The mixture was stirred at −78° for a further 1 hr, then allowed to warm to 0° and poured into satd. aq. ammonium chloride (200 ml). The mixture was stirred for 30 min then the organic phase was separated and washed with satd. aq. sodium bicarbonate and brine, dried over magnesium sulphate and concentrated in vacuo, to leave a white solid, which was recrystallised from hexane to afford the title compound (9.3 g), m.p. 58°–60°, NMR δH (CDCl$_3$) 7.3–7.0 (4H, m), 2.55–2.3 (1H, m), 2.4–2.3 (2H, m), 2.15 (3H, s), 2–1.75 (5H, m), 1.6–1.45 (2H, m), 1.25–1.0 (2H, m).

Preparation 8

3-(4-(4-Chlorophenoxy)phenyl)-2,6-dimethylpyran-4-one

A solution of 4-(4-chlorophenoxy)phenylpropan-2-one (26 g) in acetic anhydride (100 ml) was added, over 5 min, to a vigorously stirred mixture of polyphosphoric acid (200 g) and acetic anhydride (100 ml) at 80°. After stirring for 30 min the mixture was poured into water (1 liter) and extracted with toluene (2×500 ml). The combined extracts were washed with water then satd. aq. sodium bicarbonate, dried over magnesium sulphate and evaporated to give an oil. Trituration with ether gave a yellow solid, which was recrystallised from carbon tetrachloride to afford the title compound (14.64 g), m.p. 150°–152°, NMR δH (CDCl$_3$) 6.95–7.4 (8H, m), 6.2 (1H, s), 2.3 (3H, s), 2.2 (3H, s).

The following compounds were prepared from the appropriate substituted ketones by the general procedure described for preparation 3:

(a) 3-Octyl-2,6-dimethylpyran-4-one, NMR δH (CDCl$_3$) 5.95 (1H, s), 2.25 (3H, s), 2.2 (3H, s), 2.4–1.9 (2H, m), 1.T. 6–0.8 (15H, m). (From 2-undecanone—Aldrich).

(b) 3-Cyclohexyl-2,6-dimethylpyran-4-one, NMR δH (CDCl$_3$) 5.95 (1H, s), 2.3 (3H, s), 2.15 (3H, s), 2–0.9 (11H, m). (From cyclohexylacetone—Lancaster Synthesis).

(c) 3-Cyclohexylmethyl-2,6-dimethylpyran-4-one.

(d) 3-trans-(4-t-Butylcyclohexyl)-2,6-dimethylpyran-4-one, NMR δH (CDCl$_3$) 5.9 (1H, s), 2.28 (3H, s), 2.15 (3H, s), 0.85 (9H, s), 2.7–0.8 (10H, m).

(e) 3-trans-(4-(4-Chlorophenyl)cyclohexyl)-2,6-dimethylpyran-4-one, m.p. 148°–150°, NMR δH (CDCl$_3$) 7.3–7.1 (4H m), 6.0 (1H, s), 2.8–2.5 (2H, m), 2.4–2.15 (2H, m), 2.32 (3H, s), 2.18 (3H, s), 2–1.85 (2H, m), 1.7–1.35 (4H, m).

(f) 2,6-Dimethyl-3-phenylpyran-4-one, m.p. 70°–75°. (Previously reported by R. L. Letsinger and J. D. Jamison, J. Org. Chem., 193, 1961).

(g) 3-(4-Chlorophenyl)-2,6-dimethylpyran-4-one, m.p. 93°–95°, NMR δH (CDCl$_3$) 7.4–6.9 (4H, m), 6.1 (1H, s), 2.3 (3H, s), 2.2 (3H, s).

(h) 3-(3,4-Dichlorophenyl)-2,6-dimethylpyran-4-one, m.p. 132°–136°, NMR δH (CDCl$_3$) 7.48 (1H, d, J 9 Hz), 7.33 (1H, d, J 1.5 Hz), 7.08 (1H, dd, J 9, 1.5 Hz), 6.19 (1H, s), 2.28 (3H, s), 2.2 (3H, s).

(i) 3-(2,4-Dichlorophenyl)-2,6-dimethylpyran-4-one, NMR δH (CDCl$_3$) 7.45 (1H, m), 7.3–7.0 (2H, m), 6.15 (1H, s), 2.3 (3H, s), 2.1 (3H, s).

(j) 3-(4-Trifluoromethylphenyl)-2,6-dimethylpyran-4-one, m.p. 120°–123°, NMR δH (CDCl$_3$) 7.68 (2H, m), 7.38 (2H, m), 6.22 (1H, s), 2.29 (3H, s), 2.18 (3H, s).

(k) 3-(4-Fluorophenyl)-2,6-dimethylpyran-4-one, m.p. 116°–118°, NMR δH (CDCl$_3$) 7.3–7.0 (4H, m), 6.2 (1H, s), 2.28 (3H, s).

(l) 3-(4-Methoxyphenyl)-2,6-dimethylpyran-4-one, m.p. 97°–99°, NMR δH (CDCl$_3$) 7.05 (4H, m), 6.18 (1H, s), 3.78 (3H, s), 2.28 (3H, s), 2.15 (3H, s).

(m) 3-(4-(3-Chlorophenoxy)phenyl)-2,6-dimethylpyran-4-one, NMR δH (CDCl$_3$) 7.35–6.75 (8H, m), 6.15 (1H, s), 2.25 (3H, s), 2.2 (3H, s).

(n) 3-(4-(3-Trifluormethylphenoxy)phenyl)-2,6-dimethylpyran-4-one, NMR δH (CDCl$_3$) 7.45–6.85 (8H, m), 6.15 (1H, s), 2.25 (3H, s), 2.15 (3H, s).

(o) 3-(4-(4-Fluorophenoxy)phenyl)-2,6-dimethylpyran-4-one, NMR δH (CDCl$_3$) 7.3–7.1 (2H, m), 7.1–6.9 (6H, m), 6.2 (1H, s), 2.28 (3H, s), 2.2 (3H, s).

(p) 3-(4-(4-Methoxyphenoxy)phenyl)-2,6-dimethylpyran-4-one, NMR δH (CDCl$_3$) 7.2–6.6 (8H, m), 6.1 (1H, s), 3.8 (3H, s), 2.3 (3H, s), 2.2 (3H, s).

(q) 2,6-Dimethyl-3-(4-(4-methylthiophenoxy)phenyl)-pyran-4-one, NMR δH (CDCl$_3$) 7.35–7.1 (4H, m), 7.1–6.9 (4H, m), 6.2 (1H, s), 2.48 (3H, s), 2.28 (3H, s), 2.2 (3H, s).

(r) 3-(4-(3,4-Dichlorohenoxy)phenyl)-2,6-dimethylpyran-4-one, NMR δH (CDCl$_3$) 7.55–6.8 (7H, m), 6.25 (1H, s), 2.3 (3H, s), 2.2 (3H, s).

(s) 3-(4-(3,5-Dichlorophenoxy)phenyl)-2,6-dimethylpyran-4-one.

(t) 3-(4-(2,4-Dichlorophenoxy)phenyl)-2,6-dimethylpyran-4-one, NMR δH (CDCl$_3$) 7.5–6.6 (7H, m), 6.15 (1H, s), 2.25 (3H, s), 2.2 (3H, s).

(u) 3-(4-(4-Chlorophenylthio)phenyl)-2,6-dimethylpyran-4-one, NMR δH (CDCl$_3$) 7.5–7.0 (8H, m), 6.2 (1H, s), 2.24 (3H, s), 2.16 (3H, s).

(v) 2,6-Dimethyl-3-(4-biphenylyl)pyran-4-one, m.p. 188°–190°, NMR δH (d$_6$-DMSO) 8.1–7.3 (9H, m), 6.4 (1H, s), 2.6 (3H, s), 2.5 (3H, s).

(w) 3-(4′-Fluoro-4-biphenylyl)-2,6-dimethylpyran-4-one, NMR δH (d$_6$-DMSO) 7.8–7.65 (4H, m), 7.4–7.25 (4H, m), 6.22 (1H, s), 2.3 (3H, s), 2.2 (3H, s).

(x) 3-(3-(4-Chlorophenoxy)phenyl)-2,6-dimethylpyran-4-one, m.p. 114°–116°, NMR δH (d$_6$-DMSO) 7.45–7.2 (3H, m), 7.1–6.8 (5H, m), 6.2 (1H, s), 2.28 (3H, s), 2.2 (3H, s).

(y) 3-(4-(5-Trifluormethylpyrid-2yloxy)phenyl)-2,6-dimethylpyran-4-one, NMR δH (CDCl$_3$) 8.45 (1H, s), 7.9 (1H, d, J 9 Hz), 7.25 (4H, m), 7.0 (1H, d, J 9 Hz), 6.2 (1H, s), 2.28 (3H, s), 2.24 (3H, s).

(ai) 3-(4-(4-Chlorophenylsulphonyl)phenyl)-2,6-dimethylpyran-4-one, m.p. 183°–185°, NMR δH (CDCl$_3$) 8.0–7.85 (4H, m), 7.55–7.35 (4H, m), 6.18 (1H, s), 2.3 (3H, s), 2.18 (3H, s).

(bi) 3-(4-(4-Chlorophenacyl)phenyl)-2,6-dimethylpyran-4-one, NMR δH (CDCl$_3$) 7.9–7.75 (4H, m), 7.5–7.35 (4H, m), 6.25 (1H, s), 2.3 (3H, s), 2.2 (3H, s).

(ci) 3-(4-(4-Chlorobenzyl)phenyl)-2,6-dimethylpyran-4-one, NMR δH (CDCl$_3$) 7.3–6.9 (8H, m), 6.1 (1H, s), 3.9 (2H, s), 2.2 (3H, s), 2.1 (3H, s).

(di) 3-(4-(4-Chlorodifluorobenzyl)phenyl)-2,6-dimethylpyran-4-one, NMR δH (CDCl$_3$) 7.95–7.25 (8H, m), 6.25 (1H, s), 2.3 (3H, s), 2.2 (3H, s).

(ei) 3-(3-Chloro-4-(4-chlorophenoxy)phenyl)-2,6-dimethylpyran-4-one, NMR δH (CDCl$_3$) 7.4–7.25 (3H, m), 7.1 (1H, dd, J 1, 7 Hz), 7.02–6.9 (3H, s), 6.2 (1H, s) 2.3 (3H, s), 2.2 (3H, s).

(fi) 3-(4'-Chloro-4-biphenylyl)-2,6-dimethylpyran-4-one, m.p. 151°–153°.

(gi) 3-(4-Trifluoromethylphenoxy)-2,6-dimethylpyran-4-one, m.p. 104°–105°, NMR δH (CDCl$_3$) 6.95–7.8 (8H m), 6.2 (1H s), 2.3 (3H, s), 2.2 (3H, s).

(hi) 3-(4-(3-Trifluoromethoxyphenoxy)phenyl)-2,6-dimethylpyran-4-one, NMR δH (CDCl$_3$) 7.3–6.7 (8H,m); 6.2 (1H,s); 2.3 (3H,s); 2.25 (3H,s).

(ii) 2,6-Dimethyl-3-(2-pyridyl)pyran-4-one, NMR δH (CDCl$_3$) 8.7–8.4 (1H, m), 7.8–6.9 (3H, m), 6.1 (1H, s), 2.22 (3H, s), 2.18 (3H, s)

Preparation 9

3-(4-(4-Trifluoromethylphenoxy)phenyl)-2,6-dimethylpyran-4-one

A solution of 1-(4-(4-trifluoromethylphenoxy)phenyl)propan-2-one (54.5 g) in acetic anhydride (100 ml) was added, over 5 min, to a vigorously stirred mixture of polyphosphoric acid (200 g) and acetic anhydride (100 ml) at 80°. After stirring for 30 min the warm mixture was poured into water (1 liter). The solution was stirred for 30 min then extracted with toluene (3×500 ml). The combined extracts were washed with water then satd. aq. sodium bicarbonate, dried over magnesium sulphate and concentrated in vacuo to give an oil. Trituration with ether afforded the title compound as a yellow solid (18.20 g), m.p. 86°–7°, NMR δH (CDCl$_3$) 6.95–7.8 (8H, m), 6.2 (1H, s), 2.3 (3H, s), 2.2 (3H, s).

Preparation 10

3-(4-(4-trifluoromethoxyphenoxy)phenyl)-2,6-dimethylpyran-4-one

To a vigorously stirred mixture of polyphosphoric acid (60 g) and acetic anhydride (26 ml) at 90° was added over 15 min a solution of 4-(4-trifluoromethoxyphenoxy) phenylpropan-2-one (9.3 g) in acetic anhydride (30 ml). The mixture was stirred for a further 30 min at 90° then poured into water (1 liter) and extracted with toluene (2×500 ml). The combined extracts were washed with water then satd. aq. sodium bicarbonate and dried over magnesium sulphate. Concentration in vacuo gave an orange oil which was chromatographed on silica gel, eluting with dichloromethane then 1:19 methanol/dichloromethane, to give the title compound as an oil (4.1 g), NMR δH (CDCl$_3$) 6.9–7.4 (8H, m), 6.16 (1H, s), 2.24 (3H, s), 2.16 (3H, s).

Preparation 11

2,6-Dimethyl-3-(4-(4-methylsulphonylphenoxy)phenyl)pyran-4-one

To a stirred solution of 2,6-dimethyl-3-(4-(4-methylthiophenoxy)phenyl)pyran-4-one (6.22 g) in acetic acid (70 ml) at room temperature was added hydrogen peroxide (15 ml; 30% w/v). After 36 hr the mixture was poured into water and extracted with dichloromethane (2×100 ml). The combined extracts were washed with water, satd. aq. sodium bicarbonate and an aq. solution of sodium sulphite, dried over magnesium sulphate and concentrated in vacuo to leave a white solid. Recrystallisation from acetone afforded the title compound (3.39 g), m.p. 170°–173°, NMR δH (d$_6$-DMSO) 7.95–7.85 (2H, m), 7.35–7.2 (2H, m), 7.2–7.05 (4H, m), 3.05 (3H, s), 2.3 (3H, s), 2.22 (3H, s).

Preparation 12

3-(2-Pyridyl)propan-2-one

This was prepared from 2-methylpyridine, butyllithium and N,N-dimethylacetamide according to the procedure of R. Cassity, L. T. Taylor and J. F. Wolfe, J. Org. Chem., 43(11), 2286, (1986).

EXAMPLE 1

3-(4-(4-Chlorophenoxy)phenyl)-2,6-dimethyl)pyridin-4(1 H)-one 3-4-(4-Chlorophenoxy)phenyl)-2,6-dimethylpyran-4-one (10 g) was heated at 150° with 0.880 aq. ammonia (200 ml) in a stainless steel autoclave for 18 hr. After cooling the precipitate was filtered off, washed with water, dried in air and recrystallised from DMF to afford the title compound (6.6 g), m.p. 271–273°, NMR δH (d$_6$-DMSO) 7.42 (2H, m), 7.18 (2H, m), 6.95–7.1 (4H, m), 5.95 (1H, s), 2.2 (3H, s), 2.1 (3H, s).

EXAMPLE 2

3-Bromo-5-(4-(4-chlorophenoxy)phenyl-2,6-dimethylpyridin-4(1H)-one

To a stirred solution of 3-(4-(4-chlorophenoxy)phenyl)-2,6-dimethylpyridin-4(1H)-one (6.5 g) in acetic acid (50 ml) was added dropwise, over 30 min, a solution of bromine (1.2 ml) in acetic acid (10 ml). After 3 hr the mixture was poured into 1% aq. sodium sulphite (250 ml). The white precipitate was filtered, washed with water, dried in air and recrystallised from DMF (125 ml) to afford the title compound (6.6 g), m.p. 306°–308°, NMR δH (d$_6$-DMSO) 11.3 (1H, br.s), 7.42 (2H, m), 7.2 (2H, m), 6.95–7.12 (4H, m), 2.42 (3H, s), 2.1 (3H, s).

EXAMPLE 3

3-Chloro-5-(4-(4-chlorophenoxy)phenyl)-2,6-dimethylpyridin-4(1H)-one

To a stirred solution of 3-(4-(4-chlorophenoxy)phenyl)-2,6-dimethylpyridin-4(1H)-one (0.8 g) in acetic acid (10 ml) was added N-chlorosuccinimide (0.39 g). The mixture was heated at 100° for 30 min, cooled to room temperature and the precipitate filtered and dried in vacuo to afford the title compound (0.33 g), m.p. 340°–343°, NMR δH (d$_6$-DMSO) 11.3 (1H, br.s), 7.42 (2H, m), 7.2 (2H, m), 6.95–7.12 (4H, m), 2.4 (3H, s), 2.1 (3H, s).

EXAMPLE 4

3-(4-(4-Trifluoromethylphenoxy)phenyl)-2,6-dimethylpyridin-4(1H)-one 3-(4-(4-Trifluoromethylphenoxy)phenyl)-2,6-dimethylpyran-4-one (2–4 g) was heated at 150° with 0.880 aqueous ammonia (30 ml) in an autoclave for 18 hours. After cooling the precipitate was filtered off, washed with water, dried in air and recrystallised from DMF to yield the title compound as fine colourless crystals (1.4 g). M.p. 258°–260°, NMR δH (d$_6$-DMSO) 7.70 (2H, dd, J 5, 0.5 Hz), 7.0–7.3 (6H, m), 5.97 (1H, s), 2.2 (3H, s), 2.1 (3H, s).

EXAMPLE 5

3-Bromo-5-(4-(4-trifluoromethylphenoxy)phenyl)-2,6-dimethylpyridin-4(1H)-one

To a stirred suspension of 3-(4-(4-trifluoromethylphenoxy)phenyl)-2,6-dimethyl pyridin-4(1H)-one (4.12 g) in chloroform (50 ml) at room temperature was added N-bromosuccinimide (2.25 g). After 2 hr the mixture was filtered and the solid washed with chloroform and dried in vacuo. Recrystallisation from DMF afforded the title compound (2.18 g), m.p. 304°–305°, NMR δH (d$_6$-DMSO) 7.70 (2H, dd, J 5, 0.5 Hz), 7.0–7.3 (6H, m), 2.42 (3H, s), 2.1 (3H, s).

EXAMPLE 6

3-(4'-Chloro-4-biphenylyl)-2,6-dimethylpyridin-4(1H)-one

This was prepared from 3-(4'-chloro-4-biphenylyl)-2,6-dimethylpyran-4-one in a similar manner to example 1. M.p. >350° (decomp.), NMR δH (d$_6$-DMSO) 7.55–7.75 (4H, m), 7.45–7.55 (2H, m), 7.2–7.3(2H, m), 5.95 (1H, s), 2.2 (3H, s), 2.1 (3H, s).

EXAMPLE 7

3-Bromo-5-(4'-chloro-4-biphenylyl)-2,6-dimethylpyridin-4(1H)-one

This was prepared from 3-(4'-chloro-4-biphenylyl)-2,6-dimethylpyridin-4(1H)-one in a similar manner to example 2. M.p. 300° (decomp.), NMR δH (d$_6$-DMSO) 7.6–7.8 (4H, m), 7.45–7.55 (2H, m), 7.22–7.35 (2H, m), 2.4 (3H, s), 2.15 (3H, s).

EXAMPLE 8

3-Chloro-5-(4'-chloro-4-biphenylyl)-2,6-dimethylpyridin-4(1H)-one

This was prepared from 3-(4'-chloro-4-biphenylyl)-2,6-dimethylpyridin-4(1H)-one in a similar manner to example 3. M.p. >350° (decomp.), NMR δH (d$_6$-DMSO) 7.6–7.8 (4H, m), 7.45–7.55 (2H, m), 7.22–7.35 (2H, m), 2.4 (3H, s), 2.15 (3H, s).

EXAMPLE 9

5-Iodo-2,6-dimethyl-3-octylpyridin-4(1H)-one

To a stirred solution of 2,6-dimethyl-3-octylpyridin-4(1H)-one (1.17 g) and iodine (0.63 g) in ethanol (15 ml) at 70° was added dropwise a solution of iodic acid (0.22 g) in water (1 ml). After 30 min the mixture was allowed to cool and a few drops of an aqueous sodium sulphite solution added to remove excess iodine. The precipitate was filtered, washed with ethanol and recrystallised from DMF to give the title compound (0.93 g), m.p. 224°–226°, NMR δH (d$_6$-DMSO) 2.42 (3H, s), 2.3–2.5 (2H, m), 2.2 (3H, s), 1.1–1.45 (12H, m), 0.85 (3H, t).

EXAMPLE 10

5-Cyano-2,6-dimethyl-3-octylpyridin-4(1H)-one

A mixture of 5-iodo-2,6-dimethyl-3-octylpyridin-4(1H)-one (0.54 g) and cuprous cyanide (0.4 g) in pentan-1-ol was stirred and refluxed for 12 hr. After cooling the solvent was evaporated in vacuo and the residue chromatographed on silica gel, eluting with 1:19 methanol/dichloromethane to afford the title compound (0.11 g), m.p. 205°–206°, NMR δH (d$_6$-DMSO) 11.7 (1H, br.s), 2.38 (3H, s), 2.2–2.5 (2H, m), 2.25 (3H, s), 1.1–1.45 (12H, m), 0.85 (3H, t).

EXAMPLE 11

3-(4-Chlorophenyl)-1,2,6-trimethylpyridin-4-one 3-(4-Chlorophenyl)-2,6-dimethylpyran-4-one (2.27 g) was heated at 150° with a solution of methylamine in ethanol (35 ml; 33% w/w) in an autoclave for 12 hr. The mixture was concentrated in vacuo, triturated with ether and filtered, to afford the title compound (1.2 g), m.p. 221°–222°, NMR δH (d$_6$-DMSO) 7.42 (2H, d, J 5 Hz), 7.1 (2H, d, J 5 Hz), 6.1 (1H, s), 3.5 (3H, s), 2.32 (3H, s), 2.15 (3H, s).

EXAMPLE 12

3-Bromo-5-(4-Chlorophenyl)-1,2,6-trimethylpyridin-4-one

To a stirred solution of 3-(4-chlorophenyl)-1,2,6-trimethylpyridin-4-one (0.5 g) in acetic acid (5 ml) was added dropwise a solution of bromine (0.1 ml) in acetic acid (1 ml). After 5 min the mixture was poured into water. The solid was filtered off, washed with water and recrytallised from ethanol (10 ml) to give the desired compound (0.25 g), m.p. 264°–266°, NMR δH (CDCl$_3$) 7.3–7.4 (2H, m), 7.05–7.2 (2H, m), 6.95–7.12 (4H, m), 3.65 (3H, s), 2.7 (3H, s), 2.2. (3H, s).

EXAMPLE 13

3-(4-(4-Trifluoromethoxyphenoxy)phenyl)-2,6-dimethylpyridin-4(1H)-one 3-(4-(4-Trifluoromethoxyphenoxy)phenyl)-2,6-dimethylpyran-4-one (4.1 g) was dissolved in ethanol (10 ml) and heated in a stainless steel autoclave with 0.880 ammonia (35 ml) at 150° for 24 hr. After cooling the crystalline precipitate was filtered off, washed with ethyl acetate and dried in vacuo to afford the title compound (2.78 g), m.p. 244°–248°, NMR δH (d$_6$-DMSO) 11.1 (1H, br. s) 7.4 (2H, m), 7.1–7.3 (4H, m), 7.02 (2H, m), 5.95 (1H, s), 2.2 (3H, s), 2.08 (3H, s).

EXAMPLE 14

3-Bromo-5-(4-(4-trifluoromethoxyphenoxy)phenyl)-2,6-dimethylpyridin-4(1H)-one

This was prepared in a similar manner to example 5 from 3-(4-(4-trifluoromethoxyphenoxy)phenyl)-2,6-dimethylpyridin-4(1H)-one, m.p. 284°–286°, NMR δH (d$_6$-DMSO) 7.3–7.45 (2H, m), 7.1–7.3 (4H, m), 7–7.1 (2H, m), 2.45 (3H, s), 2.12 (3H, s).

EXAMPLE 15

3-Chloro-5-(4-(4-trifluoromethoxyphenoxy)phenyl)-2,6-dimethylpyridin-4(1H)-one

A mixture of 3-(4-(4-trifluoromethoxyphenoxy)phenyl)-2,6-dimethylpyridin-4(1H)-one (0.37 g) and N-chlorosuccinimide (0.16 g) in chloroform was stirred at room temperature for 3 days. The precipitate was filtered off and recrystallised from DMF to afford the title compound (0.1 g), m.p. 298°–302°, NMR δH (d$_6$-DMSO) 7.35–7.5 (2H, m), 7.1–7.3 (4H, m), 7–7.1 (2H, m), 2.38 (3H, s), 2.1 (3H, s).

EXAMPLE 16

3-Bromo-2,6-dimethyl-5-(4-(4-methylsulphinylphenoxy)phenyl)pyridine-4-one

To a stirred solution of 2,6-dimethyl-3-(4-(4-methylthiophenoxy)phenyl)pyridine-4-one (1 g) in acetic acid (10 ml) was added dropwise a solution of bromine (0.34 ml) in acetic acid (5 ml). After 1 hr a few drops of an aq. sodium sulphite solution was added to discharge excess bromine. The mixture was then poured into water, the precipitate filtered, dried and recrystallised from DMF to afford the title compound (0.57 g), m.p. 262°–263°, NMR δH (d₆-DMSO) 7.8–7.65 (2H, m), 7.3–7.15 (4H, m), 7.15–7.05 (2H, m), 2.75 (3H, s), 2.4 (3H, s), 2.1 (3H, s).

The following compounds wherein $R^1$ is hydrogen, $R^3$ and $R^4$ are both methyl and $R^5$ is hydrogen were prepared in an analogous manner to Example 1, the remaining compounds by a method analogous to Examples 2 and 3.

| Example No. | $R^1$ | $R^2$ | M.p./°C. |
|---|---|---|---|
| 17 | Br | 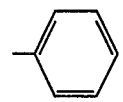 | 280–5 |
| 18 | Cl | | 338–40 |
| 19 | H | 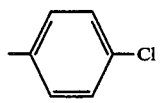 | 316–9 |
| 20 | Br | | 320–1 |
| 21 | Cl | | >330 (dec) |
| 22 | Br | 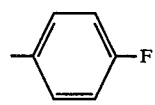 | 276–8 |
| 23 | Cl | | 361–4 |
| 24 | Br | 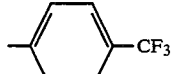 | 315–317 |
| 25 | H | 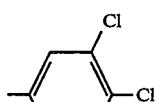 | 310–13 |
| 26 | Br | | 301–3 |
| 27 | Cl | | 325–8 |
| 28 | H | 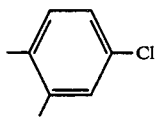 | 246–8 |
| 29 | Br | | 320–1 |
| 30 | Br | 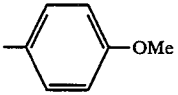 | 296–8 |
| 31 | H | | 246–8 |
| 32 | H | 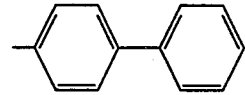 | >340 (dec.) |
| 33 | Br | | 308–11 |
| 34 | H | 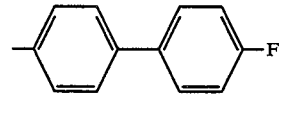 | >340 (dec.) |
| 35 | Br | | >330 (dec.) |
| 36 | Cl | | >330 (dec.) |
| 37 | H | 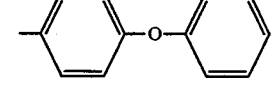 | 293–6 |
| 38 | Br | | 291–3 |

-continued

| Example No. | $R^1$ | $R^2$ | M.p./°C. |
|---|---|---|---|
| 39 | Br | | 319–21 |
| 40 | H | | 275–77 |
| 41 | H | | 261–3 |
| 42 | Br | | 299–300 |
| 42a | Cl | | 265–8 |
| 43 | H | | 272–6 |
| 44 | Br | | 292–4 |
| 45 | H | | >325 (dec.) |
| 46 | Br | | >330 (dec.) |
| 47 | Cl | | >345 (dec.) |
| 48 | H | | 247–50 |
| 49 | Br | | 260–3 |
| 50 | H | | 268–70 (dec.) |
| 51 | Br | | 256–60 |
| 52 | Br | | >300 (dec.) |
| 53 | Cl | | >320 (dec.) |
| 54 | Br | | 326–7 |
| 55 | H | | |
| 56 | H | $C_8H_{17}$ | 130–2 |
| 57 | Br | | 250–5 |
| 58 | Cl | | 222–4 |
| 59 | H | | 314–6 |
| 60 | Br | | 278–81 |
| 61 | H | | 249–50 |
| 62 | Br | | 310–12 |
| 63 | H | | 342–4 |
| 64 | Br | | 289–90 |

| Example No. | R¹ | R² | M.p./°C. |
|---|---|---|---|
| 65 | H | *trans*-4-(4-chlorophenyl)cyclohexyl | 334–9 |
| 66 | Br | *trans*-4-(4-chlorophenyl)cyclohexyl | 323–6 |
| 67 | Cl | *trans*-4-(4-chlorophenyl)cyclohexyl | 358–60 |
| 68 | H | 4-(4-methoxyphenoxy)phenyl | 278–280 |
| 69 | Br | 4-(4-methoxyphenoxy)phenyl | 300–303 |
| 70 | H | 4-(4-methylthiophenoxy)phenyl | 253–255 |
| 71 | Br | 4-(4-methylsulfinylphenoxy)phenyl | 262–263 |
| 72 | H | 4-(4-methylsulfonylphenoxy)phenyl | 303–305 |
| 73 | Br | 4-(4-methylsulfonylphenoxy)phenyl | 308–310 |
| 74 | H | 4-(3-chlorophenoxy)phenyl | 232–234 |
| 75 | Br | 4-(3-chlorophenoxy)phenyl | 286–290 |
| 76 | Cl | 4-(3-chlorophenoxy)phenyl | 268–272 |
| 77 | H | 4-(3,4-dichlorophenoxy)phenyl | 288–291 (dec.) |
| 78 | Br | 4-(3,4-dichlorophenoxy)phenyl | 313–315 |
| 79 | Cl | 4-(3,4-dichlorophenoxy)phenyl | 333–335 |
| 80 | H | 4-(3,5-dichlorophenoxy)phenyl | 299–301 (dec.) |
| 81 | Br | 4-(3,5-dichlorophenoxy)phenyl | 305–308 |
| 81a | Cl | 4-(3,5-dichlorophenoxy)phenyl | 340–344 (dec.) |
| 82 | H | 4-(2,4-dichlorophenoxy)phenyl | 294–298 |
| 83 | Br | 4-(2,4-dichlorophenoxy)phenyl | 323–324 (dec.) |
| 84 | Cl | 4-(2,4-dichlorophenoxy)phenyl | 317–319 (dec.) |
| 85 | Br | 4-(4-chlorobenzyl)phenyl | 314–315 |
| 86 | Br | 4-[(4-chlorophenyl)difluoromethyl]phenyl | 287–289 |
| 87 | H | pyridyl | 252–253 |

EXAMPLE 88

3-(4-(3-Trifluoromethoxyphenoxy)phenyl)-2,6-dimethylpyridin-4(1H)-one

This was prepared from 3-(4-(3-Trifluoromethoxyphenoxy)phenyl)-2,6-dimethyl pyran-4-one in a similar manner to example 13. m.p. 244°–246°, Nmr δH (d₆-DMSO) 11.1 (1H, br. s) 7.5 (2H, m), 7.25–7.0 (7H, m), 5.95 (1H, s), 2.2 (3H, s), 2.08 (3H, s).

EXAMPLE 89

3-Bromo-5-(4-(3-trifluoromethoxyphenoxy)phenyl)-2,6-dimethylpyridin-4(1H)-one

This was prepared in a similar manner to example 5 from 3-(4-(3-trifluoromethoxyphenoxy)phenyl)-2,6-dimethylpyridin-4(1H)-one m.p. 274°–277°, Nmr δH (d₆-DMSO) 7.6–7.45 (1H, m), 7.3–7.0 (7H, m), 2.45 (3H, s), 2.1 (3H, s).

EXAMPLE 90

3-Chloro-5-(4-3-trifluoromethoxyphenoxy)phenyl)-2,6-dimethylpyridin-4(1H)-one

A mixture of 3-(4-(3-trifluoromethoxyphenoxy)phenyl)-2,6-dimethylpyridin-4(1H)-one (1 g) and N-chlorosuccinimide (0.43 g) in chloroform (30 ml) was stirred and refluxed for 5 hours. After cooling to room temperature the precipitate was filtered off and recrystallised from DMF to afford the title compound (0.23 g), m.p. 249°–253°, Nmr δH (d₆-DMSO) 11.6 (1H, br s), 7.6–7.5 (1H, m), 7.3–7.05 (7H, m), 2.4 (3H, s), 2.1 (3H, s).

EXAMPLE 91

3-Bromo-2,6-dimethyl-4-methoxy-5-[4-(4-trifluoromethoxyphenoxy)phenyl]pyridine

A mixture of 3-Bromo-5-(4-(3-trifluoromethoxyphenoxy)phenyl)-2,6-dimethyl pyridin-4(1H)-one (1.5 g), potassium carbonate (0.33 g) and methyl iodide (2 ml) in dry DMF (25 ml) was stirred at room temperature for 24 hours. The mixture was diluted with water and extracted with chloroform, washed with water, dried over magnesium sulphate and evaporated in vacuo. The residue was chromatographed on silica, eluting with 99:1 dichloromethane:methanol, to give the title compound (0.4 g), m.p. 39°–41°, Nmr δH (CDCl3) 7.3–7.0 (8H, m), 3.7 (3H, s), 2.7 (3H, s), 2.3 (3H, s).

EXAMPLE 92

4-Acetoxy-3-chloro-2,6-dimethyl-5-[4-(4-trifluoromethoxyphenoxy)phenyl]pyridine

To a stirred suspension of 3-Chloro-5-(4-(4-trifluoromethoxyphenoxy)phenyl)-2,6-dimethyl pyridin-4(1H)-one (0.41 g) in dry DMF, under nitrogen, was added all at once sodium hydride (0.05 g of a 60% dispersion in mineral oil). After stirring at rt for 30 min acetyl chloride (0.14 ml) was added. The mixture was stirred at rt for a further 2 hr, poured into iced water, extracted with ether, washed with water and satd. aq. sodium bicarbonate and dried over magnesium sulphate. Evaporation gave an oil which was triturated with hexane to give the title compound (0.2 g), m.p. 78°–80°, Nmr δH (CDCl3) 7.3–7.0 (8H, m), 2.68 (3H, s), 2.35 (3H, s), 2.05 (3H, s).

EXAMPLE 93

3-(4-(4-Chlorophenoxy)phenyl)-1-hydroxy-2,6-dimethylpyridin-4-one

A mixture of 3-(4-(4-chlorophenoxy)phenyl)-2,6-dimethylpyran-4-one (1.0 g), hydroxylamine hydrochloride (1.06 g), sodium acetate (1.25 g) and water (5 ml) in ethanol (10 ml) was heated at reflux for 3 days. After cooling to rt the mixture was diluted with water (20 ml) and the precipitate filtered off and washed with ethyl acetate. Recrystallisation from DMF afforded the title compound (0.2 g), m.p. 232°–236°, NMR δH (d6-DMSO)7.5–7.4 (2H, d, a 8 Hz), 7.3–7.2 (2H, d, J 8 Hz), 7.15–7.0 (4H, m), 6.75 (1H, s), 2.35 (3H, s), 2.15 (3H, s).

EXAMPLE 94

3-Bromo-5-(4-(4-chlorophenoxy)-1-hydroxy-2,6-dimethylpyridin-4-one

To a stirred solution of 3-(4-(4-chlorophenoxy)phenyl)-1-hydroxy-2,6-dimethyl pyridin-4-one (0.5 g) in acetic acid (10 ml) was added dropwise a solution of bromine (0.08 ml) in acetic acid (1 ml). After 1.5 hour a few drops of an aq. sodium sulphite solution was added to discharge excess bromine. The mixture was diluted with water and the precipitate filtered, washed with water, dried and recrystallised from DMF to afford the title compound (0.32 g), m.p. 246°–250° (dec.), NMR δH (d6-DMSO) 7.5–7.4 (2H,d, J 8 Hz), 7.25–7.15 (2H,d, J 8 Hz), 7.15–7.0 (4H,m), 2.6 (3H,s), 2.1 (3H,s).

EXAMPLE 95

3-Bromo-2,6-dimethyl-5-[4-(4-trifluoromethoxyphenoxy)phenyl]-4-pyridinyl diethyl phosphate To a solution of 3-Bromo-5-(4-(4-trifluoromethoxyphenoxy)phenyl)-2,6-dimethyl pyridin-4(1H)-one (4.44 g) in dry DMF (30 ml) under nitrogen was added sodium hydride (0.39 g of a 60% dispersion in mineral oil). After stirring at rt for 30 min diethyl chlorophosphate (2.1 ml) was added dropwise. The mixture was stirred at rt for 48 hr then filtered. The filtrate was diluted with toluene (200 ml), washed with 2M sodium carbonate, dried over magnesium sulphate and concentrated in vacuo. The residue was chromatographed on silica, eluting with 1:4 ethyl acetate:dichloromethane to afford the title compound (1.22 g), m.p. 80°–81°, NMR δH (CDCl3) 7.35–7.0 (8H, m), 4–3.8 (4H, m), 2.7 (3H, s), 2.25 (3H, s), 1.25–1.15 (6H, 2×t).

Parmaceutical Formulations

The following examples illustrate, pharmaceutical formulations which may be employed in accordance with the present invention:

A. Injectable solution

A solution for intramuscular injection may be prepared by mixing:

| | |
|---|---|
| Compound of formula (I) | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

B. Injectable solution

| | |
|---|---|
| Compound of formula (I) | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

C. Tablet

| | |
|---|---|
| Compound of formula (I) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

D. Oral suspension

| | |
|---|---|
| Compound of formula (I) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

E. Injectable suspension

| | |
|---|---|
| Compound of formula (I) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

F. Capsule

| | |
|---|---|
| Compound of formula (I) | 100 mg |
| Starch 1500 | 150 mg |
| Magnesium stearate | 2.5 mg |
| filled into a hard gelatin capsule | |

Biological Test Results

1. In vitro Activity vs. *Plasmodium falciparum*

The in vitro activity of the test compounds was determined using a modification of the semi-automated microdilution technique of Desjardins et al (1979). Initial dilutions were prepared from 1/100th molecular weight (in mg) of the compounds dissolved in dry ethanol, with the first 1:100 dilution being in ethanol and subsequent dilutions in RPMI 1640 medium supplemented with 10% v/v human plasma. Serial 1:2 drug dilutions were prepared in microtitration trays using microdiluters, each dilution being set up in triplicate. To this was added RPMI 1640 medium supplemented with 10% v/v human plasma, fresh and infected type A Rhesus positive human erythrocytes to yield a haematocrit of 3% and a parasitaemia of 0.25–0.5%. [$^3$H]-hypoxanthine was added to give a final concentration of 12.5–16 μCi/ml of culture. The plates were sealed and incubated in a modular incubator in a gas mixture of 5% $O_2$; 3% $CO_2$ and 92% $N_2$ by volume at 37° C. The test was completed as described by Desjardins et at (1979). Data were analysed to yield $IC_{50}$ values by best fit to a sigmoidal dose-response curve. The results are given in Table 1 below.

TABLE 1

| In vitro activity vs Plasmodium falciparum | | |
|---|---|---|
| Compound of Example No: | $IC_{50}$ ($\mu$M) | No. of tests |
| 1 | 2.5 | (4) |
| 2 | 0.2 | (17) |
| 3 | 1.4 | (2) |
| 4 | 1.1 | (1) |
| 5 | 0.22 | (9) |
| 6 | 8.4 | (4) |
| 7 | 2.0 | (2) |
| 8 | 0.5 | (9) |
| 10 | 2.3 | (1) |
| 12 | 23.5 | (1) |
| 14 | 0.023 | (6) |
| 15 | 0.02 | (5) |
| 16 | 1.6 | (1) |

2. In vivo Activity vs. *P.yoelii* in the Mouse

In vivo activity was determined using the modified 4-day suppressive test involving an infection of the YM strain of *P.yoelii* by $3 \times 10^6$ parasitized erythrocytes/ml and 7 oral doses given in 4 days in CD1 mice. Drugs were formulated by ball milling overnight in 0.25% celacol with stainless steel balls to form a fine particle suspension. The total requirement was formulated at the beginning of a test and thereafter stored at 4° C. On the morning of day 5 smears of tail blood were prepared from each mouse, the parasitaemias counted and the inhibition as compared to control animals calculated. Data were analysed to yield $ED_{50}$ values by the best fit to a sigmoidal dose response curve, and the results are presented in Table 2 below.

TABLE 2

| Mouse 4-day suppressive test vs *P. yoelii* | | |
|---|---|---|
| Compound of Example No: | $ED_{50}$ (mg/kg) | No. of tests |
| 1 | 2.5 | (1) |
| 2 | 0.7 | (2) |
| 3 | 1.6 | (1) |
| 4 | 1.25 | (1) |
| 5 | 0.26 | (2) |
| 6 | 1.6 | (1) |
| 7 | 1.4 | (1) |
| 8 | 0.6 | (4) |
| 12 | 16.4 | (1) |
| 14 | 0.34 | (1) |
| 15 | 0.19 | (1) |

We claim:

1. A compound of formula (I):

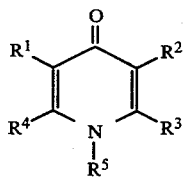

wherein
$R^1$ represents a hydrogen or halogen atom, or a cyano group;
$R^2$ represents a carbocyclic group having 6 to 10 ring atoms and containing at least one aromatic ring; or a heterocyclic group selected from furyl, thienyl and pyridyl, said carbocyclic and heterocyclic groups being optionally substituted by a substituent selected from halogen, cyano, nitro, amino, mono- or di$C_{1-4}$alkylamino, $C_{1-4}$alkyl, halo$C_{1-4}$alkyl, $C_{1-4}$alkoxy, $C_{1-4}$alkylsulphonyl, $C_{1-4}$alkylthio, $C_{1-4}$alkanoyl, pyridyl optionally substituted by halo$C_{1-4}$alkyl, pyridyloxy, optionally substituted by halo$C_{1-4}$alkyl or the carbocyclic or heterocyclic group $R^2$ is optionally substituted by a group

wherein
X represents —O—,

S(O)m, —CH$_2$O—, —OCH$_2$—, CH$_2$S(O)m, —S(O)mCH$_2$—, —CYZ(CH$_2$)p or —(CH$_2$)pCYZ, or X is a single bond linking the phenyl groups;
Y and Z independently represent hydrogen, halogen or $C_{1-4}$alkyl;
$R^6$ represents halogen, cyano, nitro, amino, mono- or di-($C_{1-4}$) alkylamino, $C_{1-4}$alkyl, halo($C_{1-4}$)alkyl, $C_{1-4}$alkoxy or halo($C_{1-4}$)alkoxy, or S(O)$_m C_{1-4}$ alkyl;
n is zero or an integer from 1 to 5;
m is zero, one or two; and
p is zero or one;
the carbocyclic or heterocyclic group $R^2$ being optionally further substituted by one or two substituents selected from halogen, cyano, nitro, amino, mono- or di-($C_{1-4}$)alkylamino, $C_{1-4}$alkyl, halo($C_{1-4}$)alkyl, $C_{1-4}$alkoxy, and $C_{1-4}$alkylthio;
or $R^2$ represents a $C_{3-6}$cycloalkyl group or a $C_{3-6}$cycloalkyl-$C_{1-6}$alkyl group, wherein the cycloalkyl group or moiety is optionally substituted by $C_{1-6}$alkyl, $C_{3-6}$cycloalkyl or by a phenyl group which may itself be optionally substituted by ($R^6$)n as defined above;
or $R^2$ represents a $C_{1-10}$alkyl group, optionally substituted by hydroxy or $C_{1-6}$alkoxy, or by a carbocyclic or heterocyclic group as defined above;
$R^3$ and $R^4$, which may be the same or different, each represent a hydrogen or halogen atom, or a $C_{1-6}$alkyl group optionally substituted by 1 to 3 halogen atoms; and
$R^5$ represents a hydrogen atom, a hydroxyl group, or a $C_{1-6}$alkyl group, optionally substituted by hydroxy, carboxy, amino or mono- or di-($C_{1-4}$)alkyl amino,
provided that:
(i) when $R^1$ is cyano, $R^3$ and $R^4$ are both hydrogen and $R^5$ is methyl, ethyl, acetoxy or hydroxy, $R^2$ is not a phenyl group or a phenyl group substituted by a substituent selected from halogen, nitro, $C_{1-4}$alkyl, $C_{1-2}$alkoxy, $C_{1-2}$alkylthio or $C_{1-2}$alkylsulphonyl
(ii) when $R^1$ is cyano $R^3$ and $R^4$ are both hydrogen, $R^5$ is methyl, ethyl, acetoxy or hydroxy and $R^2$ is a phenyl group substituted by a group

X is not —OCH$_2$—, —S(O)$_m$CH$_2$—, —CYZ(CH$_2$)$_p$— or —(CH$_2$)$_p$CYZ—, where Y and Z are both hydrogen or one of Y and Z is methyl and the other is hydrogen (iii) when R$^1$ is hydrogen, R$^3$ and R$^4$ are both hydrogen and R$^5$ is methyl, R$^2$ is not a phenyl group substituted in the 3 position relative to the pyridone ring by a substituent selected from halogen, nitro, C$_{1-4}$alkyl, haloC$_{1-4}$alkyl, C$_{1-4}$alkoxy, C$_{1-4}$alkylthio or C$_{1-4}$alkylsulphonyl;

(iv) when R$^1$ is hydrogen, R$^3$ and R$^4$ are both hydrogen, R$^5$ is methyl and R$^2$ is a phenyl group substituted in the 3 position relative to the pyridone ring by a group

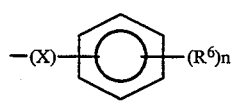

X is not —O—, S(O)$_m$, —OCH$_2$— or a single bond linking the phenyl groups;

(v) when R$^1$ is hydrogen, R$^3$ is methyl, R$^4$ is C$_{1-6}$alkyl and R$^5$ is hydrogen or methyl, R$^2$ is not methyl;

(vi) when R$^1$ is hydrogen, R$^3$ and R$^4$ are both methyl and R$^5$ is hydrogen, R$^2$ is not propyl;

(vii) when R$^1$ is hydrogen and R$^3$ and R$^4$ are both methyl, R$^2$ is not an unsubstituted phenyl group;

or a salt or other physiologically functional derivative thereof.

2. A compound of formula (IB):

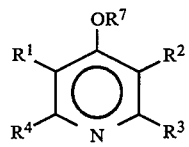

wherein
R$^1$ represents a hydrogen or halogen atom, or a cyano group;

R$^2$ represents a carbocyclic group having 6 to 10 ring atoms and containing at least one aromatic ring; or a heterocyclic group selected from furyl, thienyl and pyridyl, said carbocyclic and heterocyclic groups being optionally substituted by a substituent selected from halogen, cyano, nitro, amino, mono- or diC$_{1-4}$alkylamino, C$_{1-4}$alkyl, haloC$_{1-4}$alkyl, C$_{1-4}$alkoxy, C$_{1-4}$alkylsulphonyl, C$_{1-4}$alkylthio, C$_{1-4}$alkanoyl, pyridyl, optionally substituted by haloC$_{1-4}$alkyl, pyridyloxy, optionally substituted by haloC$_{1-4}$alkyl or the carbocyclic or heterocyclic group R$^2$ is optionally substituted by a group

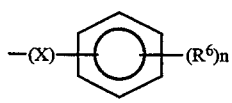

wherein
X represents —O—,

S(O)m, —CH$_2$O—, —OCH$_2$—, —CH$_2$S(O)m, —S(O)mCH$_2$—, —CYZ(CH$_2$)p or —(CH$_2$)pCYZ, or X is a single bond linking the phenyl groups;

Y and Z independently represent hydrogen, halogen or C$_{1-4}$alkyl;

R$^6$ represents halogen cyano, nitro, amino, mono- or di-(C$_{1-4}$)alkylamino, C$_{1-4}$alkyl, halo(C$_{1-4}$)alkyl, C$_{1-4}$alkoxy or halo(C$_{1-4}$)alkoxy, or S(O)$_m$C$_{1-4}$alkyl;

n is zero or an integer from 1 to 5;

m is zero, one or two; and p is zero or one;

the carbocyclic or heterocyclic group R$^2$ being optionally further substituted by one or two substituents selected from halogen, cyano, nitro, amino, mono- or di(C$_{1-4}$)alkylamino, C$_{1-4}$alkyl, halo(C$_{1-4}$)alkyl, alkoxy and C$_{1-4}$alkylthio;

or R 2 represents a C$_{3-6}$cycloalkyl group or a C$_{3-6}$cycloalkyl- C$_{1-6}$alkyl group, wherein the cycloalkyl group or moiety is optionally substituted by C$_{1-6}$alkyl, C$_{3-6}$cycloalkyl or by a phenyl group which may itself be optionally substituted by (R$^6$)n as defined above;

or R$^2$ represents a C$_{1-10}$alkyl group optionally substituted by hydroxy or C$_{1-6}$alkoxy, or by a carbocyclic or heterocyclic group as defined above;

R$^3$ and R$^4$, which may be the same or different, each represent a hydrogen or halogen atom, or a C$_{1-6}$alkyl group optionally substituted by 1 to 3 halogen atoms; and R$^7$ represents a C$_{1-6}$alkyl group; a group OC(O)R$^2$ wherein R$^2$ represents a C$_{1-6}$alkyl group; or a group —OP(O)(OR$^9$)(OR$^{10}$), wherein R$^9$ and R$^{10}$, which may be the same or different, each represent hydrogen or a C$_{1-6}$alkyl group.

3. A compound according to claim 1 wherein R$^1$ is a hydrogen atom or a halogen atom.

4. A compound according to claim 1 wherein R$^2$ is a C 3–6 cycloalkyl group, optionally substituted by a C$_{1-6}$alkyl group or by a phenyl group, which itself may be optionally substituted by a halogen; or R$^2$ is an aromatic carbocyclic group optionally substituted by one or two halogen atoms, or by a C$_{1-4}$alkoxy, halo C$_{1-4}$alkyl, phenyl, phenoxy, phenylsulphonyl, phenylthio, benzyl, α,α-difluorobenzyl, benzoyl or pyridyloxy group, wherein a phenyl or pyridyl group or moiety in the aforementioned substituents may itself be optionally substituted by one or two substituents selected from halo; haloC$_{1-4}$alkyl; C$_{1-4}$alkoxy; haloC$_{1-4}$alkoxy; or S(O)mC$_{1-4}$alkyl wherein m is zero, one or two.

5. A compound according to claim 1 wherein R$^2$ is an aromatic carbocyclic group optionally substituted by phenyl, pyridyl, halogen, cyano, nitro amino mono-or di-(C$_{1-4}$)alkyl-amino, C$_{1-4}$alkyl, halo-(C$_{1-4}$)alkyl, C$_{1-4}$alkoxy, phenoxy, C$_{1-4}$alkylsulphonyl, C$_{1-4}$alkylthio, C$_{1-4}$alkanoyl, phenylsulphonyl, phenylthio or benzoyl, wherein a phenyl group or moiety or a pyridyl group in the aforementioned substitutents may itself be further optionally substituted by halogen, cyano, nitro, amino, mono- or di(C$_{1-4}$)alkylamino, C$_{1-4}$alkyl, halo-(C$_{1-4}$)alkyl, C$_{1-4}$alkoxy, halo(C$_{1-4}$)alkoxy, or —S(O)$_m$ C$_{1-4}$alkyl, where m is zero, 1 or 2.

6. A compound according to claim 1 wherein R$^3$ and R$^4$ each represent a C$_{1-6}$alkyl group.

7. A compound according to claim 1 wherein R$^5$ is a hydrogen atom.

8. A compound according to claim 1 of formula (IC)

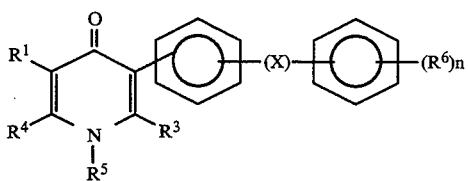 (IC)

wherein
R¹ represents halogen;
R³ and R⁴, which may be the same or different each represent a $C_{1-4}$alkyl group;
R⁵ represents a hydrogen atom;
X represents —O—,

S(O)m, —CH₂O—, —OCH₂—, —CH₂S(O)$_m$—, —S(O)mCH₂—, —CYZ(CH₂)p or —(CH₂)pCYZ, or X is a single bond linking the phenyl groups;

Y and Z independently represent hydrogen, halogen or $C_{1-4}$ alkyl;
R⁶ represents halogen, cyano, nitro, amino, mono- or di-($C_{1-4}$)alkylamino, $C_{1-4}$alkyl, halo($C_{1-4}$)alkyl, $C_{1-4}$alkoxy, halo($C_{1-4}$)alkoxy; or —S(O)m$C_{1-4}$alkyl;
n is zero or an integer from 1 to 5
m is zero, one or two; and
p is zero or one;
or a physiologically acceptable salt or other physiologically functional derivative thereof.

9. A compound selected from:
3-Bromo-5-[4-(4-chlorophenoxy)phenyl]-2,6-dimethylpyridin-4(1H)-one;
3-Bromo-5-[4-(4-trifluoromethylphenoxy)phenyl]-2,6-dimethylpyridin-4(1H)-one;
3-Bromo-5-(4-(4-trifluoromethoxyphenoxy)phenyl)-2,6-dimethylpyridin-4(1H)-one;
3-chloro-5-(4-(4-trifluoromethoxyphenoxy)phenyl)-2,6-dimethylpyridin-4(1H)-one;
3-Bromo-2,6-dimethyl-5-[4-(3-trifluoromethylphenoxy)phenyl]pyridin-4(1H)-one;
3-chloro-2,6-dimethyl-5-[4-(3-trifluoromethylphenoxy)phenyl]pyridin-4(1H)-one;
3-chloro-2,6-dimethyl-5-[4-(3-trifluoromethoxyphenoxy)phenyl]pyridin-4(1H)-one;
3-bromo-2,6-dimethyl-5-[4-(3-trifluoromethoxyphenoxy)phenyl]pyridin-4(1H)-one;
4-acetoxy-3-chloro-2,6-dimethyl-5-[4-(4-trifluoromethoxyphenoxy)phenyl]pyridine.

10. A therapeutic formulation comprising a compound according to claim 1 or a salt or other physiologically functional derivative thereof, together with a pharmaceutically or veterinarily acceptable carrier thereof.

11. A therapeutic formulation according to claim 10 in unit dose form.

12. A method of preventing or treating parasitic infections which comprises administering to a mammal suffering from or susceptible to a parasitic infection an effective amount of a compound of claim 1.

13. A therapeutic formulation comprising the compound according to claim 2 or a salt or other physiologically functional derivative thereof, together with a pharmaceutically or veterinarily acceptable carrier thereof.

14. A therapeutic formulation according to claim 13 in unit dose form.

15. A method of preventing or treating parasitic infections which comprises administering to a mammal suffering from or susceptible to a parasitic infection an effective amount of a compound of claim 2.

* * * * *